US012611547B2

(12) United States Patent
Wang et al.

(10) Patent No.: US 12,611,547 B2
(45) Date of Patent: Apr. 28, 2026

(54) NON-DRUG CARDIO-CEREBROVASCULAR DISEASE THERAPEUTIC APPARATUS

(71) Applicant: Biomobie (Shanghai) Regenerative Medicine Co., Ltd., Shanghai (CN)

(72) Inventors: Jian Wang, Shanghai (CN); Fan Bu, Shanghai (CN); Baoxin Wang, Shanghai (CN)

(73) Assignee: BIOMOBIE (SHANGHAI) REGENERATIVE MEDICINE CO., LTD., Shanghai (CN)

( * ) Notice: Subject to any disclaimer, the term of this patent is extended or adjusted under 35 U.S.C. 154(b) by 1111 days.

(21) Appl. No.: 17/670,782

(22) Filed: Feb. 14, 2022

(65) Prior Publication Data

US 2023/0001225 A1     Jan. 5, 2023

(30) Foreign Application Priority Data

Jun. 30, 2021    (CN) .......................... 202110734405.8

(51) Int. Cl.
*A61N 2/02* (2006.01)
*A61H 39/00* (2006.01)
(Continued)

(52) U.S. Cl.
CPC ................. *A61N 2/02* (2013.01); *A61N 2/06* (2013.01); *H03M 1/66* (2013.01)

(58) Field of Classification Search
CPC .. A61N 2/02; A61N 2/06; H03M 1/66; A61H 39/00
See application file for complete search history.

(56) References Cited

U.S. PATENT DOCUMENTS

2006/0149337 A1* 7/2006 John ................... A61N 1/37235
                                                                   607/45
2006/0187607 A1* 8/2006 Mo .......................... A61N 2/02
                                                                   361/143

(Continued)

OTHER PUBLICATIONS

Https://www.arrow.com/en/research-and-events/articles/dac-buying-guide-find-the-best-digital-to-analog-converter (Year: 2019).*

*Primary Examiner* — Carrie R Dorna
*Assistant Examiner* — Joshua Daryl D Lannu
(74) *Attorney, Agent, or Firm* — John P. White

(57) ABSTRACT

The present invention provides a non-drug cardio-cerebrovascular disease therapeutic apparatus. A waveform diagram of a pulse current for generating a pulse electromagnetic field includes four characteristic bands in a cycle range of 360° and reciprocates circularly: an abrupt-rising band T1 where a current intensity I(t) abruptly rises, wherein a highest value thereof is slightly lower than a maximum value Imax of an output current; a first slow-rising band T2 where the current intensity I(t) slowly rises to the maximum value Imax; an abrupt-decreasing band T3 where the current intensity I(t) abruptly decreases, wherein a minimum value Imin thereof is slightly higher than a minimum value (Imin) of the output current; and a slow-decreasing band T4 where the current intensity I(t) slowly decreases to the minimum value (Imin). The non-drug cardio-cerebrovascular disease therapeutic apparatus provided by the present invention can significantly improve and treat cardio-cerebrovascular diseases and achieve obvious effects.

10 Claims, 34 Drawing Sheets

(51) Int. Cl.
 *A61N 2/06* (2006.01)
 *H03M 1/66* (2006.01)

(56) References Cited

U.S. PATENT DOCUMENTS

2010/0286470 A1* 11/2010 Schneider .............. A61N 2/006
 600/14
2016/0220838 A1* 8/2016 Scheinowitz ............ A61N 2/02
2020/0309883 A1* 10/2020 Ding .................. G01R 33/4826

* cited by examiner (Waveforms in a cycle)

NON-DRUG CARDIO-CEREBROVASCULAR DISEASE THERAPEUTIC APPARATUS

CROSS-REFERENCE TO RELATED APPLICATIONS

This application claims priority of Chinese Patent Application No. 202110734405.8, filed Jun. 30, 2021, the content of which is hereby incorporated by reference into the subject application.

TECHNICAL FIELD

The present invention relates to a pulse electromagnetic field therapeutic apparatus, in particular to a therapeutic apparatus using a pulse electromagnetic field to treat cardio-cerebrovascular diseases.

BACKGROUND

In China, cardio-cerebrovascular diseases have become a first cause of death, and increased risk of coronary heart disease has seriously affected life and health of patients and brought great inconvenience to life of patients. In addition, due to increased work pressure and faster pace of life, many people suffer from severe insomnia and metabolic syndrome, which seriously affect their life and health.

Clinical studies have shown that the incidence of coronary microvascular disease (CMVD) is about 45%-60% in patients with myocardial ischemic symptoms and single-catheter coronary arteriography showing non-obstructive lesions. In 2012, a 7.5-year follow-up study of 11223 European patients with stable angina showed that nearly ⅔ of male patients and ⅓ of female patients had no obstructive coronary artery disease at the time of admission, but major cardiovascular events and national mortality of these patients were significantly higher than those of a control population. It was speculated that CMVD may be an important cause of poor prognosis. However, there are limited treatment methods for CMVD at present.

A PCT international patent application with publication number WO 2012/048203 discloses a hand-held electromagnetic wave therapy system. It discloses an electromagnetic waveform which first has an abrupt-rising initial band in one cycle, then a slow-rising band, and a band that decreases straight down to zero and continues to maintain a zero peak at one end.

A Chinese patent with publication number CN110201305A discloses a coronary heart disease therapeutic apparatus using pulse electromagnetic fields, which includes an electromagnetic wave generator that may apply a pulse electromagnetic field to a patient. The pulse electromagnetic field is: $B=kI(t)-B0$, where k is a factor 42.162, B0 is an initial magnetic field intensity, $\tau$ represents a time constant generated by a waveform generator, t represents a time (point), $(t1-t)$ represents a duration or working time of a pulse, Imax represents a maximum current passing a circuit, and a) $600\,\mu sec \le \tau \le 0.01$ sec, b) $10\,msec \le t1 \le 0.01$ sec, and c) $50\,mA \le Imax \le 100$ mA. The pulse electromagnetic field effectively treats clinical symptoms of patients with coronary heart disease.

However, the pulse electromagnetic field used by the above therapeutic apparatus cannot better treat cardiovascular diseases, and the pulse electromagnetic field thereof has insufficient effect on regeneration of human blood vessels and blood cells.

SUMMARY

The present invention aims to provide a non-drug cardio-cerebrovascular disease therapeutic apparatus in view of cardiovascular defects in the prior art. The non-drug cardio-cerebrovascular disease therapeutic apparatus includes a power supply device, a pulse current generator connected with the power supply device to generate a pulse current, and a pulse magnetic field generator connected with the pulse current generator, wherein the pulse magnetic field generator includes a magnetic head, the magnetic head includes an electromagnet and a coil, and the coil is connected with the pulse current generator and receives the pulse current to generate a pulse electromagnetic field that may be applied to a patient, wherein a waveform diagram of the pulse current includes four characteristic bands in a cycle range of 360° and reciprocates circularly:

an abrupt-rising band/section T1 where a current intensity I(t) abruptly rises, wherein a highest value after rising is slightly lower than a maximum value Imax of an output current;

a slow-rising band T2 where the current intensity I(t) slowly rises to the maximum value Imax;

an abrupt-decreasing band T3 where the current intensity I(t) abruptly decreases, wherein a minimum value Imin after abrupt decreasing is slightly higher than a minimum value (Imin) of the output current; and a slow-decreasing band T4 where the current intensity I(t) slowly decreases to the minimum value (Imin).

Further, a sequence of the pulse current in each cycle is T1, T2, T3 and T4.

Further, a waveform formula of the pulse current is:

$$I(t)=I^*(1-e^{(t/z)}), \text{ in a 0-180° interval}=I^*(e^{(t/z)}), \text{ in a 180-360° interval}$$

where:
Z is a time factor, with a range of (0.001-0.003),
f=30 Hz,
t is a time range of 0-0.03333 second, and
I is the current intensity provided by a power supply, and is 0-100 mA.

In a preferred implementation of the present invention, $0.01\ second \le \tau \le 0.025$ second.

In a preferred implementation of the present invention, $0.001 \le Z \le 0.003$.

Specially, in a preferred implementation of the present invention, Z=0.002.

In a preferred implementation of the present invention, $0\ mA \le I \le 90$ mA.

In an implementation of the present invention, an electromagnetic wave generator applies the pulse electromagnetic field to Laogong acupoint of left and right hands and/or Yongquan acupoint of left and right feet of the patient.

In an implementation of the present invention, the pulse current generator adopts an ARM processor.

In an implementation of the present invention, the apparatus further includes a digital-to-analog converter which converts a waveform digital signal sent by the ARM processor into an analog pulse current signal so that the magnetic head generates the pulse electromagnetic field.

In an implementation of the present invention, the power supply device further includes a current manager.

The non-drug cardio-cerebrovascular disease therapeutic apparatus provided by the present invention can significantly improve myocardial ischemia of patients with coronary heart disease. Because a current waveform that generates the pulse magnetic field is a pulse current waveform composed of the above waveform characteristics T1, T2, T3 and T4, the overall waveform characteristics are quite different from those of an existing magnetic field therapeutic apparatus, myocardial ischemia of the patients with coronary heart disease can be significantly improved and blood perfusion can be effectively restored. Current medical methods are limited in blood perfusion for restoring myocardial blood supply, and the non-drug cardio-cerebrovascular disease therapeutic apparatus provided by the present invention has become a new technology for high-efficiency intervention of cardiovascular diseases. Compared with the prior art, the present invention realizes essential improvements in the patients with coronary heart disease and myocardial ischemia, achieves obvious effects, and can apparently be widely used for treating or improving symptoms of overall cardio-cerebrovascular diseases.

BRIEF DESCRIPTION OF THE DRAWINGS

FIGS. 6A-18A are respectively experiment diagrams of ischemia flow (MBFQ) of subjects 1-13.

FIGS. 6B-18B are respectively experiment diagrams of ischemia flow (MBFQ) of subjects 1-13.

Descriptions corresponding to relevant English expressions in FIGS. 6A-18A and FIGS. 6B-18B: 1. RCA: right coronary artery; 2. LAD: left anterior descending coronary artery; 3. LCX: left circumflex coronary artery; 4. MFR: myocardial flow reserve.

DETAILED DESCRIPTION

The non-drug cardio-cerebrovascular disease therapeutic apparatus of the present invention will be described in details with reference to the accompanying drawings.

Figure 1:
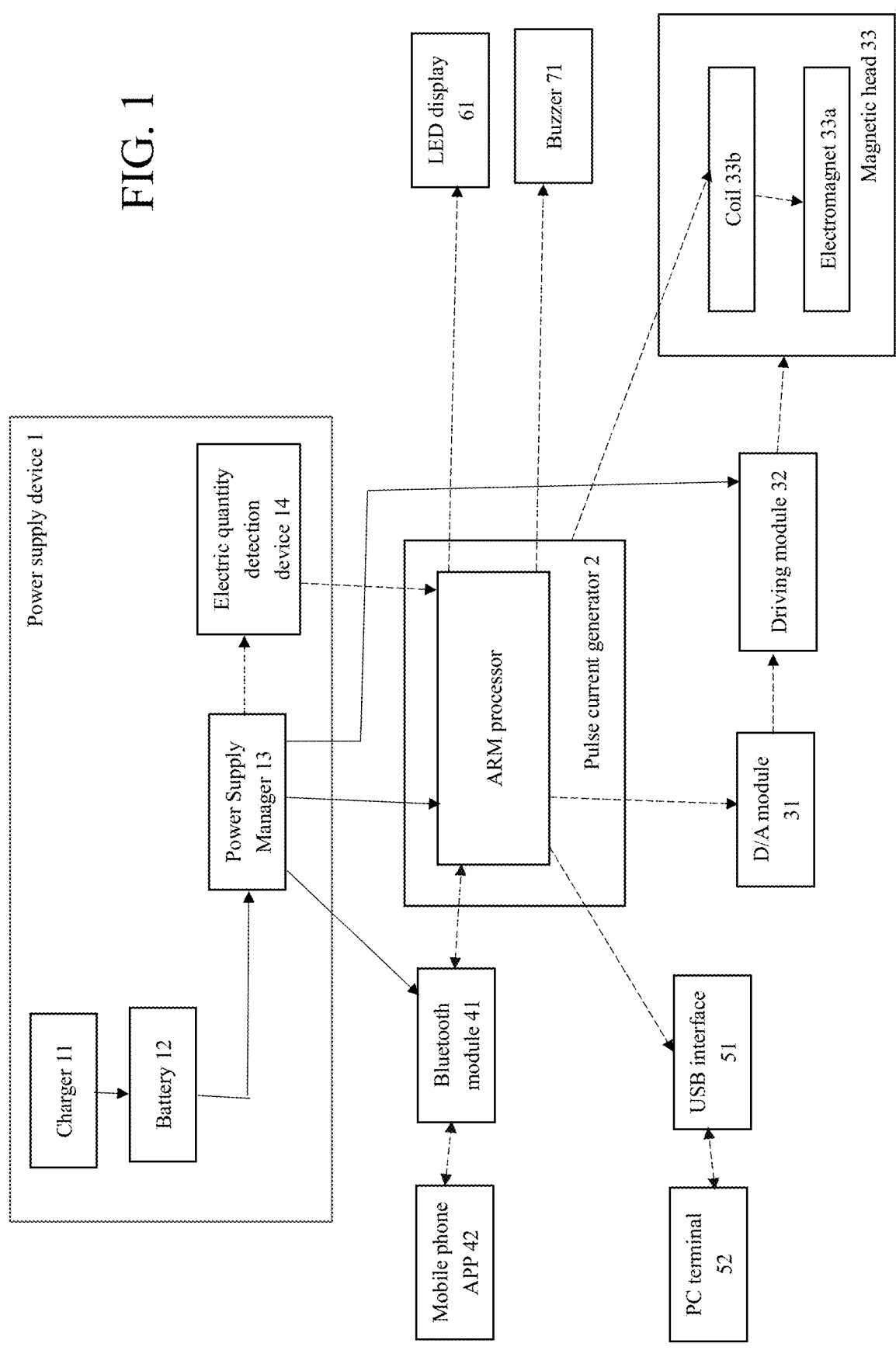
FIG. 1 is a systematic structural block diagram of an embodiment of a non-drug cardio-cerebrovascular disease therapeutic apparatus provided by the present invention.

As shown in FIG. 1, a non-drug cardio-cerebrovascular disease therapeutic apparatus provided by the present invention includes a power supply device 1, a pulse current generator 2 and a pulse magnetic field generator 3. The pulse current generator 2 is connected with the power supply device 1 to generate a pulse current, the pulse magnetic field generator 3 is connected with the pulse current generator 2 to generate a pulse magnetic field, the pulse magnetic field generator is composed of a magnetic head 33, the magnetic head 33 includes an electromagnet 33*a* and a coil 33*b*, and the coil 33*b* is connected with the pulse current generator 2 and receives the above pulse current to generate, through the electromagnet 33*a*, a pulse electromagnetic field that may be applied to a patient.

As shown in FIG. 1, in an embodiment, the power supply device 1 of the non-drug cardio-cerebrovascular disease therapeutic apparatus provided by the present invention includes a battery 12 and a power supply manager 13. The battery 12 may be connected with a charger 11 to obtain stable power. The power supply manager 13 is configured to provide electric power to the battery 12 and perform power supply management. In addition, the power supply device 1 further includes an electric quantity detection device 14, which is configured to detect an electric quantity of the battery 12. The pulse current generator 2 adopts an ARM processor (integrated block), which is connected to the power supply manager 13, receives the electric power (current) provided by the battery 12 and generates a pulse current. The ARM processor may also be connected with an APP in a mobile phone through a Bluetooth module 41 and be used in conjunction with a user's mobile phone. The ARM processor may also be connected to a PC terminal 52 through a USB interface 51. In the embodiment, the non-drug cardio-cerebrovascular disease therapeutic apparatus provided by the present invention further includes an LED display 61 and a buzzer 62. The LED display 61 may display a control or alerting signal, and the buzzer 62 may display an acoustical warning signal for being convenient for a user. Of course, the ARM processor may also adopt an integrated circuit block, such as a central processing unit (CPU), to generate a pulse current (voltage) waveform set by the present invention. The power supply manager 13 may manage electric power output by the battery 12. Its specific functions include: converting battery voltage into the power supply and reference voltage required by chips in functional modules.

The pulse magnetic field generator 3 includes a module D/A (digital-to-analog converter) 31, a driving module 32 and the magnetic head 33. The module D/A 31 converts a waveform digital signal sent by the ARM processor into an analog pulse current signal and inputs the signal to the coil of the magnetic head 33 through the driving module 32 so that the electromagnet generates the pulse electromagnetic field. In the embodiment, a function of the driving module 32 is: enhancing analog waveform power output by ARM to meet the driving power requirement of the magnetic head.

Figure 2A:
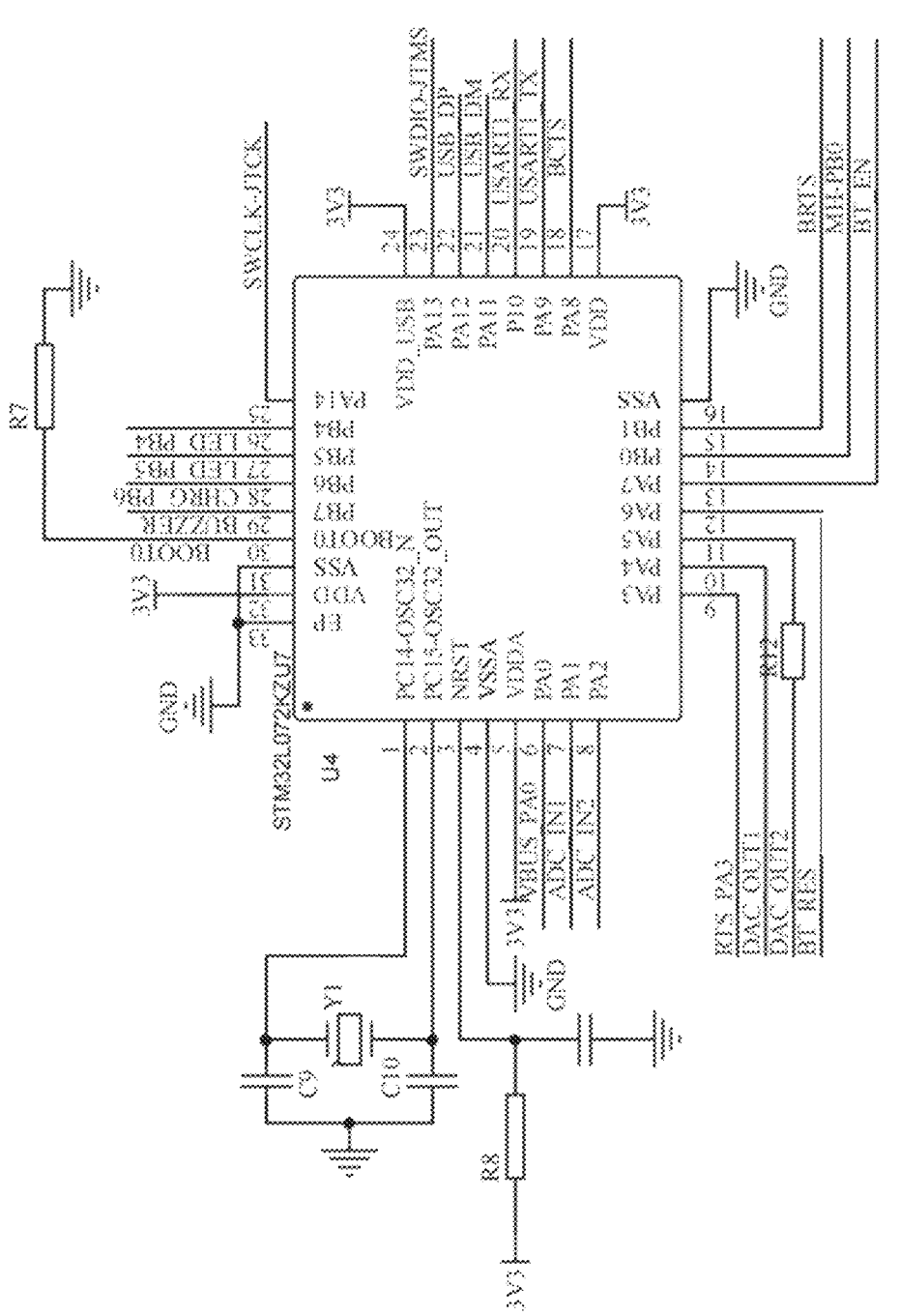
FIGS. 2A-2D are electronic circuit diagrams of an embodiment of a non-drug cardio-cerebrovascular disease therapeutic apparatus provided by the present invention.
Figure 2B:
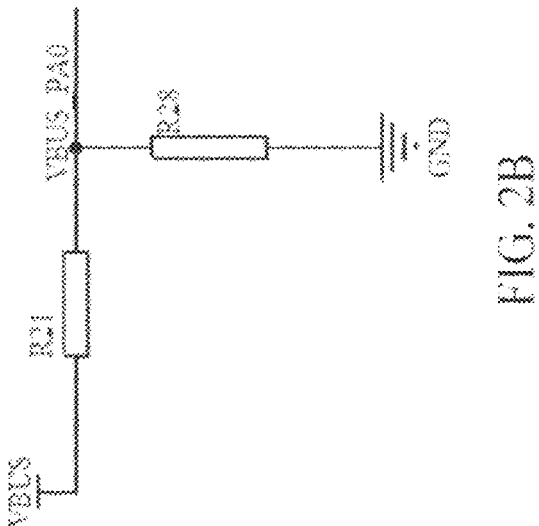
Figure 2C:
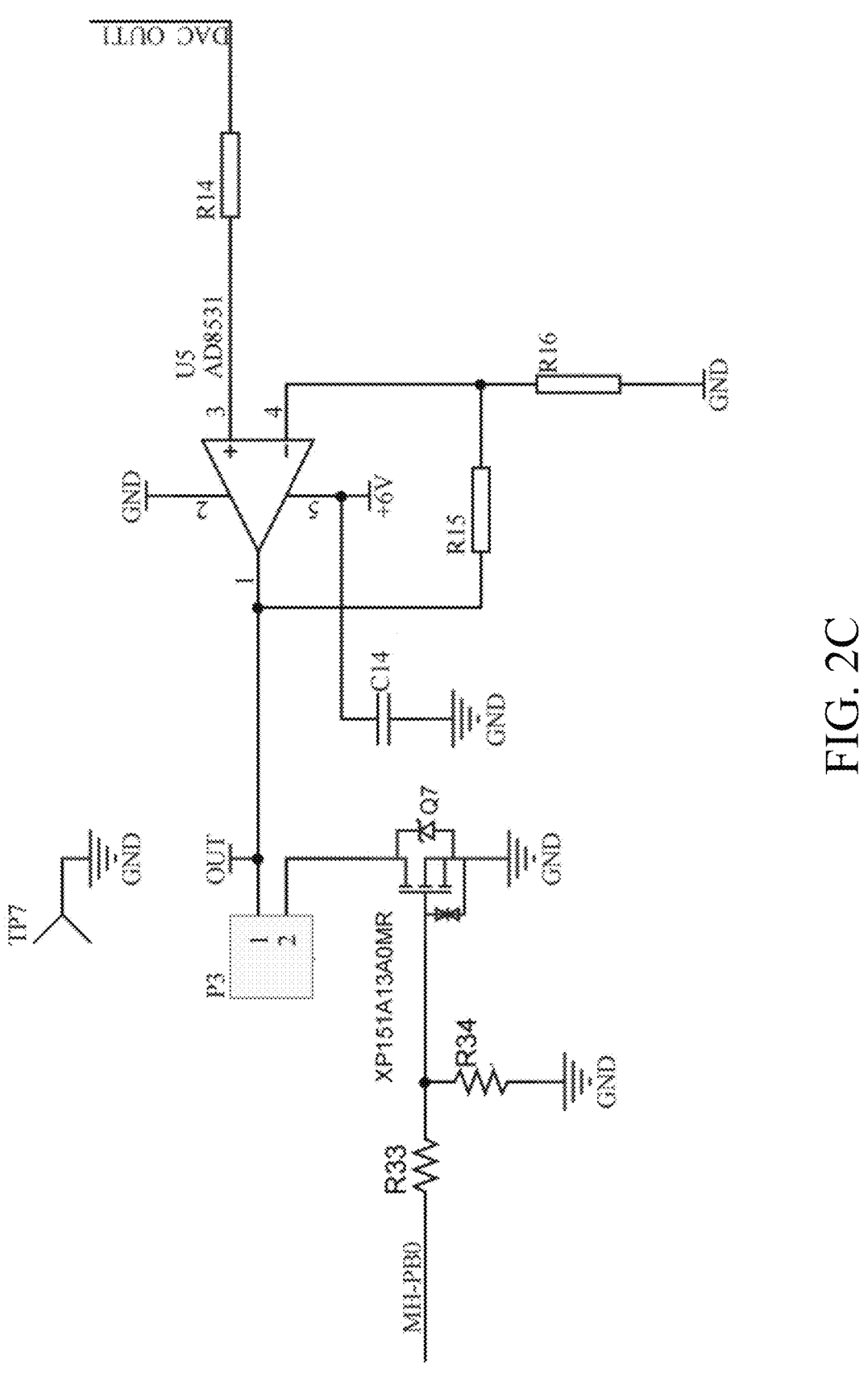
Figure 2D:
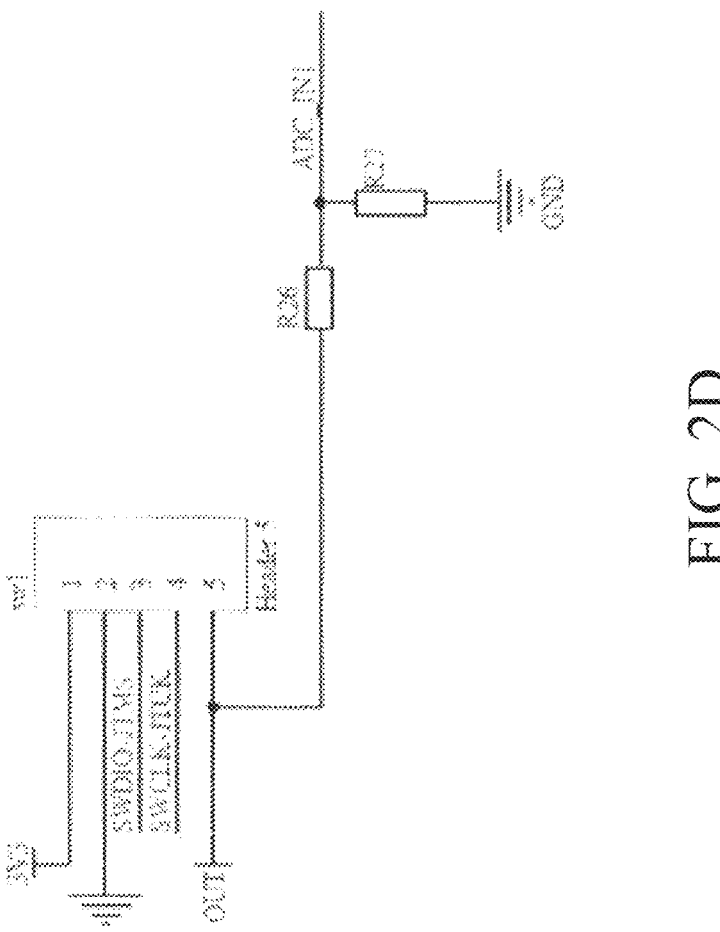

FIGS. 2A-2D are electronic circuit diagrams of an embodiment of a non-drug cardio-cerebrovascular disease therapeutic apparatus provided by the present invention. As shown in FIG. 2A, the above ARM processor adopts an integrated circuit block of model STM32F413CHU6 (manufacturer: STMicroelectronics). In the integrated circuit block, two electrodes with electrode numbers 17 and 32 are power signals of an input power source (battery 12), and two electrodes with electrode numbers 10 and PA4 output pulse voltage or current waveforms (described below). FIG. 2B is a power supply circuit. FIG. 2C is a circuit mainly for detecting a magnetic head. It mainly detects whether the magnetic head 33 is normal, so as to ensure that the magnetic head 33 may work normally. FIG. 2D is for a programming interface, with model of an integrated circuit block Header5: PIN4, manufacturer: Shenzhen Zhonghewei Technology Co., Ltd.

Figures 3, 4A:
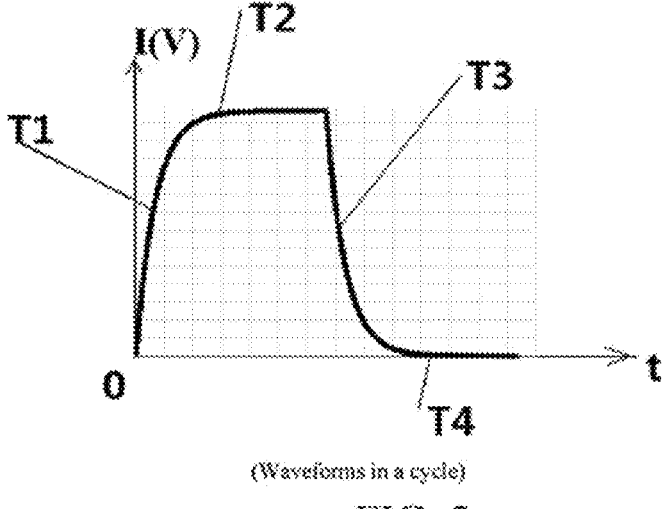
FIG. 3 is a pulse current waveform diagram of a non-drug cardio-cerebrovascular disease therapeutic apparatus provided by the present invention.
FIG. 4A is a pulse current waveform diagram of an embodiment of a non-drug cardio-cerebrovascular disease therapeutic apparatus provided by the present invention.

As shown in FIG. 3, a waveform diagram of the above pulse current includes the following four characteristic bands in a cycle range of 360° and reciprocates circularly:

an abrupt-rising band T1 where a current intensity I(t) abruptly rises, wherein a highest value after abrupt rising is slightly lower than a maximum value Imax of an output current;

then, a slow-rising band T2 where the current intensity I(t) slowly rises to the maximum value Imax;

then, an abrupt-decreasing band T3 where the current intensity I(t) abruptly decreases, wherein a minimum value after abrupt decreasing is slightly higher than a minimum value (Imin) of the output current; and finally, a slow-decreasing band T2 where the current intensity I(t) slowly decreases to the minimum value (Imin).

As shown in FIG. 4, in the embodiment, a waveform formula of the pulse current (voltage) is:

$$I(t) = I*\left(1 - e^{\wedge}\left(t/z\right)\right), \text{ in a } 0\text{--}180° \text{ interval} = I*\left(e^{\wedge}\left(t/z\right)\right),$$
$$\text{in a } 180\text{--}360° \text{ interval}$$

where:

z is a time factor, with a range of (0.001-0.003), f=30 Hz, t is a time range of 0-0.03333 second, and I is the current intensity provided by the power supply device, and is 0-100 mA.

Specifically, in FIG. 4A, an amplitude value unit of the ordinate is voltage (V), and the abscissa is time whose unit is µs (microsecond), and z=0.002.

In a preferred implementation of the present invention, $0.01 \text{ second} \leq \tau \leq 0.025$ second.

Figure 4B:
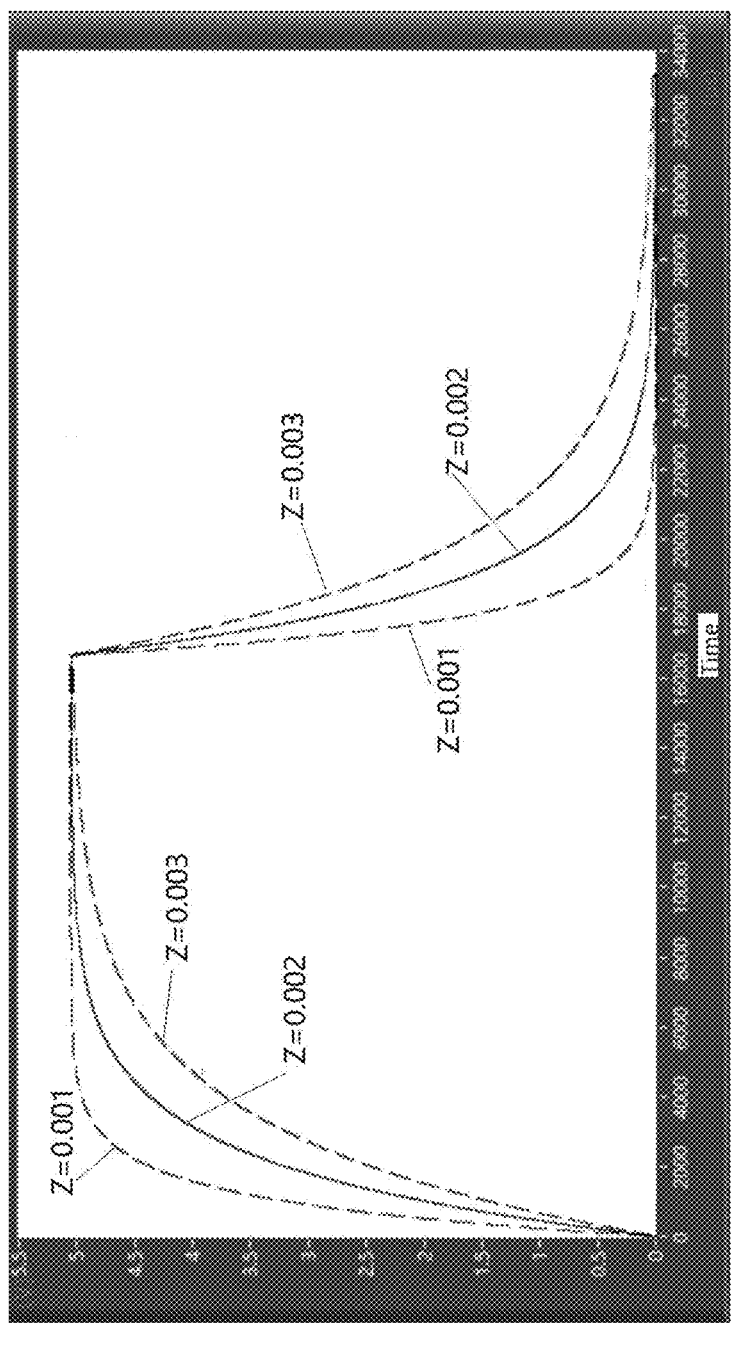
FIG. 4B is a schematic diagram showing variation range with the change of time factor z in the pulse current waveform diagram of the present invention.

In a preferred implementation of the present invention, $0.001 \leq z \leq 0.003$ (See FIG. 4B).

In a preferred implementation of the present invention, 0 $\text{mA} \leq I \leq 90$ mA.

In an implementation of the present invention, an electromagnetic field generator applies the pulse electromagnetic field to Laogong acupoint of left and right hands and/or Yongquan acupoint of left and right feet of a patient.

In the embodiment, the maximum value Imax is about 1.3 volts, and the minimum value Imin is zero or close to zero.

The above pulse current is input to the coil of the magnetic head 33, and the electromagnet generates a corresponding pulse electromagnetic field which may be configured to electromagnetically treat acupoints of a human body, treat the patient's cardio-cerebrovascular disease or improve the patient's cardio-cerebrovascular function.

Referring to FIG. 4B, a remarkable feature of the invention is that the variation range of the said characteristic bands T1, T2, T3 and T4 of the waveform diagram of pulse current can be defined or adjusted by time factor z, preferably, the variation range of z is 0.001-0.003, furthermore, when z=0.001 or 0.003, the waveform diagram of pulse current in the present invention is shown the dotted lines in FIG. 4, and the said abrupt-rising band/section T1, slow-rising band T2, abrupt-decreasing band T3 and slow-decreasing band T4 can possess better wave characteristics, thus, the pulsed electromagnetic field for treatment produced by it has achieved remarkable technical effect, and its effect is also verified by the following experimental data.

Experimental Verification

I. Experimental Verification of a Non-Drug Cardio-Cerebrovascular Disease Therapeutic Apparatus Provided by the Present Invention In the research process of the present invention, the applicant has also done a lot of experiments, comparing, analyzing and experimenting different pulse waveforms, and a pulse magnetic field generated by pulse current waveforms with the T1, T2, T3 and T4 characteristics of the present invention described above has a better therapeutic effect on cardiovascular diseases of a human body, and has an obvious therapeutic effect on the regeneration of human cells. Meanwhile, on this basis, through the following standard comparative experiments, further verification is achieved.

In a verification test, the applicant entrusted a well-known cardiovascular disease treatment hospital in China, the outpatient department of the Department of Cardiology, Fuwai Hospital of the Chinese Academy of Medical Sciences, to treat 13 patients with coronary microcirculation disorders who were in the hospital from August 2017 to December 2019 as research targets.

Inclusion criteria of the verification test: patients whose coronary angiography or coronary CTA showed 50-80% stenosis of anterior descending artery, circumflex artery, or main branch of right coronary artery and its first-level branches, and who did not undergo coronary intervention.

Exclusion criteria: patients with previous history of PCI, PTCA or CABG, myocardial bridge, cardiomyopathy, severe valvular heart disease, history of heart tumor, or congenital heart disease, or patients with ATP contraindications: patients with asthma, atrioventricular block, sinus syndrome, or sinus node insufficiency, or patients taking nicorandil.

A randomized double-blind controlled study was adopted. On the basis of taking anti-atherosclerosis drugs regularly, an old therapeutic apparatus (the applicant adopted the therapeutic apparatus produced by a WO 2012/048203 technology mentioned in the background art), the therapeutic apparatus of the present invention (with a therapeutic effect) and a comfort machine of the therapeutic apparatus of the present invention (a comfort machine without any therapeutic effect) are respectively used for an experiment group and a control group to be tested and studied. MFR before intervention with the old therapeutic apparatus and the therapeutic apparatus of the present invention (product code "R7") and 3-6 months after the intervention was detected by nuclide, and the experimental procedure met the corresponding specifications.

1. Treatment Method of Pulse Magnetic Field

A magnetic field emission part was aligned with Laogong acupoint area or Yongquan acupoint area of a subject. The pulse magnetic field was respectively applied to left and right Laogong acupoint areas once, respectively applied to left and right Yongquan acupoint areas once, and then respectively applied to left and right Laogong acupoint areas once, 8 min every time and 1 cycle every day. The course of treatment was 3-6 months.

2. Efficacy Evaluation

At baseline and after 3 months or 6 months of treatment, the subjects were examined by SPECT-CT myocardial perfusion imaging, and the percentage of area of stress myocardial ischemia was recorded.

3: Experimental Test Result

As shown in Table 1 below, experiment results of the 13 subjects (3 cases in old therapeutic apparatus experiment group: subjects 1-3; 7 cases in experiment group of the non-drug cardio-cerebrovascular disease therapeutic apparatus provided by the present invention: subjects 4-10; and 3 cases in control group: subjects 11-13) are as follows:

TABLE 1

| | Test Result Chart | | |
| --- | --- | --- | --- |
| Subject | Percentage of myocardial ischemia before treatment | Percentage of myocardial ischemia after treatment | Reduced ischemia percentage |
| Subject 1 | 10.90% | 8.46% | 22.39% |
| Subject 2 | 38.81% | 31.95% | 17.68% |
| Subject 3 | 6.35% | 5.69% | 10.39% |
| Subject 4 | 21.12% | 0.76% | 96.40% |
| Subject 5 | 10.37% | 0 | 100% |
| Subject 6 | 33.76% | 8.88% | 73.70% |
| Subject 7 | 9.52% | 0 | 100% |
| Subject 8 | 10.05% | 2.06% | 79.5% |
| Subject 9 | 8.79% | 2.21% | 74.86% |
| Subject 10 | 18.17% | 10.11% | 44.36% |
| Subject 11 | 3.24% | 12.32% | −280.25% |
| Subject 12 | 18.06% | 35.84% | −98.45% |
| Subject 13 | 59.19% | 98.51% | −66.43% |

Figure 5:
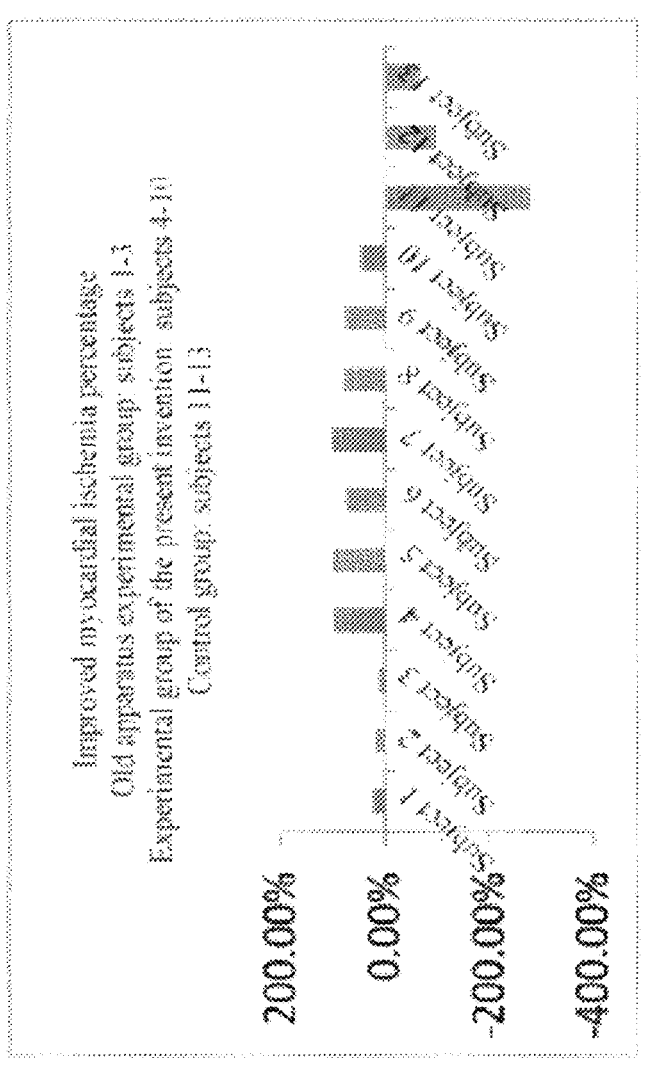
FIG. 5 is an experimental comparison diagram of a non-drug cardio-cerebrovascular disease therapeutic apparatus provided by the present invention.

As shown in FIG. 5, the above experiment results are shown in a curve chart and the effect of comparison can be seen more clearly. It can be seen that, after 3-6 months of treatment, average treatment improvement effect obtained by the subjects in the experiment group using the non-drug cardio-cerebrovascular disease therapeutic apparatus provided by the present invention is: a microcirculation ischemia range evaluated by MFR (myocardial flow reserve) of the experiment group (10 cases) adopting the therapeutic apparatus of the present invention was reduced by 81.28% on average, a microcirculation ischemia range evaluated by MFR of the test group (3 cases) adopting the old therapeutic apparatus was reduced by 16.82% on average, and a microcirculation ischemia range evaluated by MFR of the control group (3 cases) was increased by 148.43% on average.

Specific experimental data and actual experimental test images of the above 13 subjects are as follows:

Subject 1

The percentage of myocardial ischemia before using the old therapeutic apparatus for treatment was 10.9%.

The percentage of myocardial ischemia after using the old therapeutic apparatus for treatment was 8.46%.

The myocardial ischemia was reduced by 22.39% using the old therapeutic apparatus for treatment compared with that before treatment.

Figure 6A:
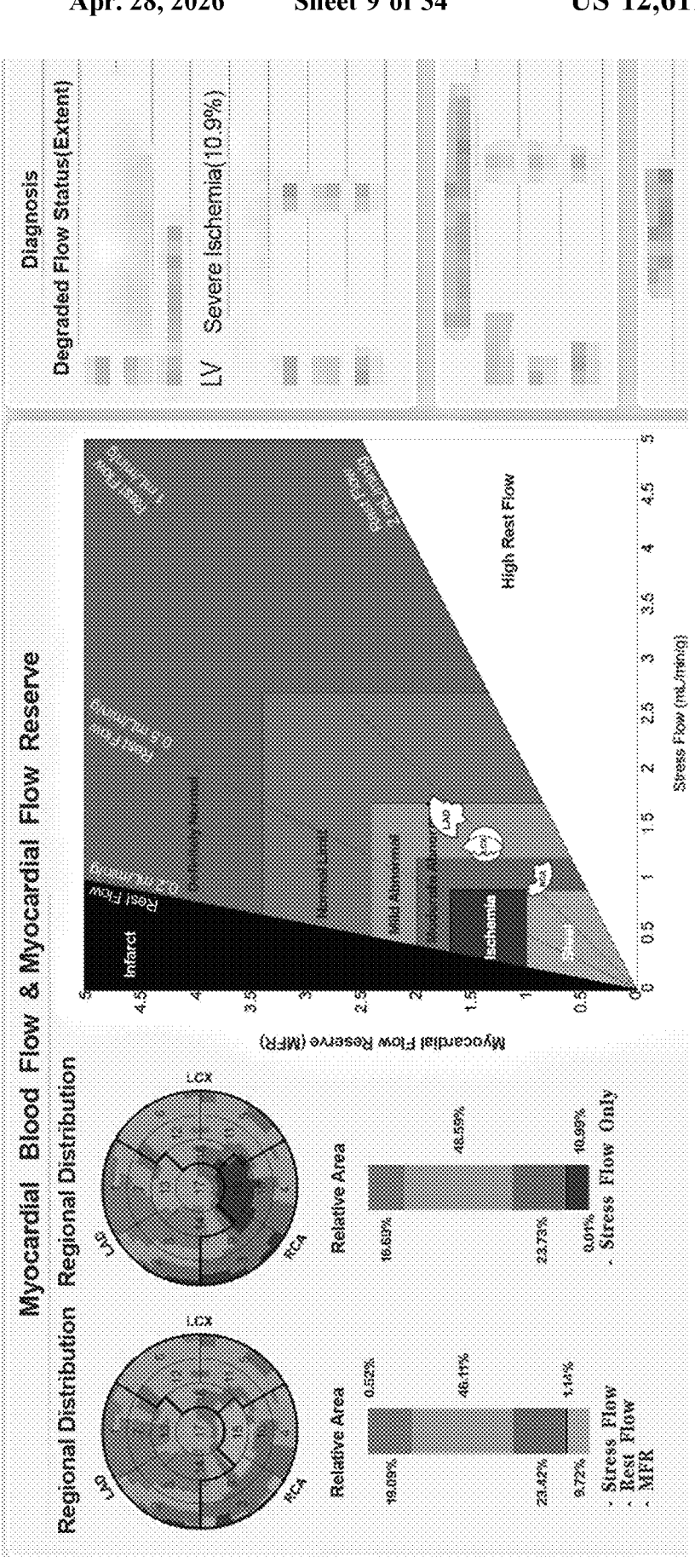

FIG. 6A is a diagram of myocardial flow reserve measured by a SPECT-CT instrument on Sep. 13, 2017. It shows that: the percentage of myocardial ischemia before using R7 for treatment was 10.9%.

Figure 6B:
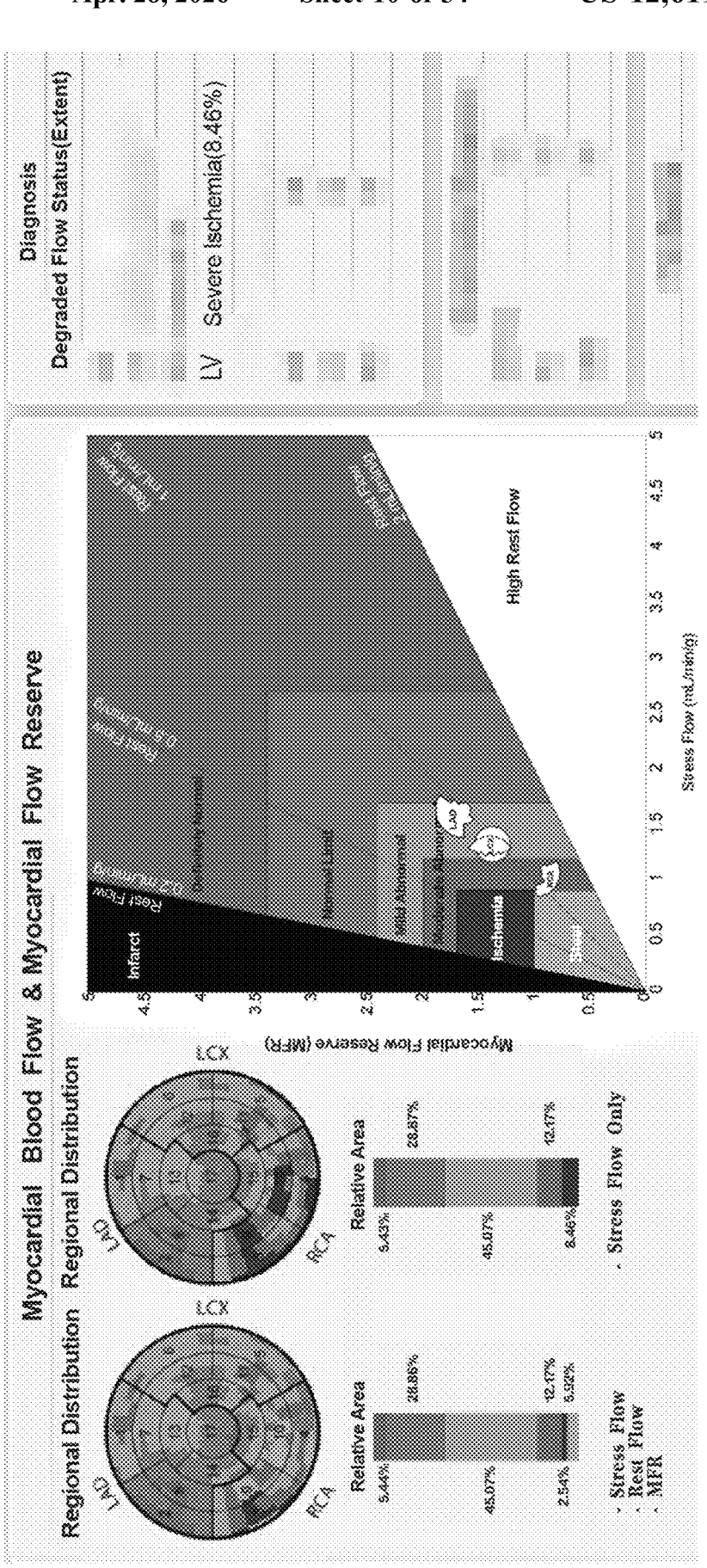

FIG. 6B is a diagram obtained by a SPECT-CT instrument on Dec. 12, 2017. It shows that the percentage of myocardial ischemia after using R7 for treatment was 8.46%.

Subject 2

The percentage of myocardial ischemia before using the old therapeutic apparatus for treatment was 38.81%.

The percentage of myocardial ischemia after using the old therapeutic apparatus for treatment was 31.95%.

The myocardial ischemia was reduced by 17.68% using the old therapeutic apparatus for treatment compared with that before treatment.

Figure 7A:
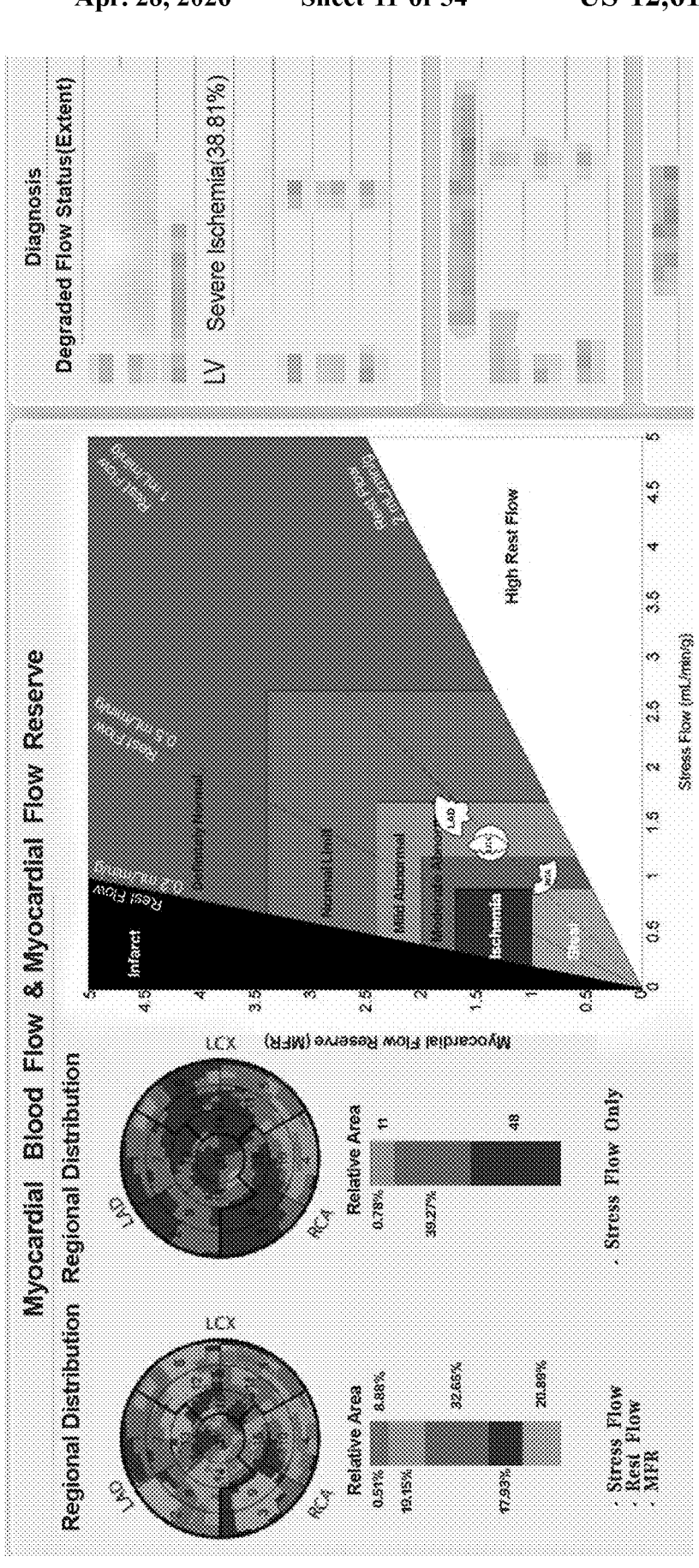

FIG. 7A is a diagram of myocardial flow reserve measured by a SPECT-CT instrument on Aug. 10, 2017. It shows that: the percentage of myocardial ischemia before using R7 for treatment was 38.81%.

Figure 7B:
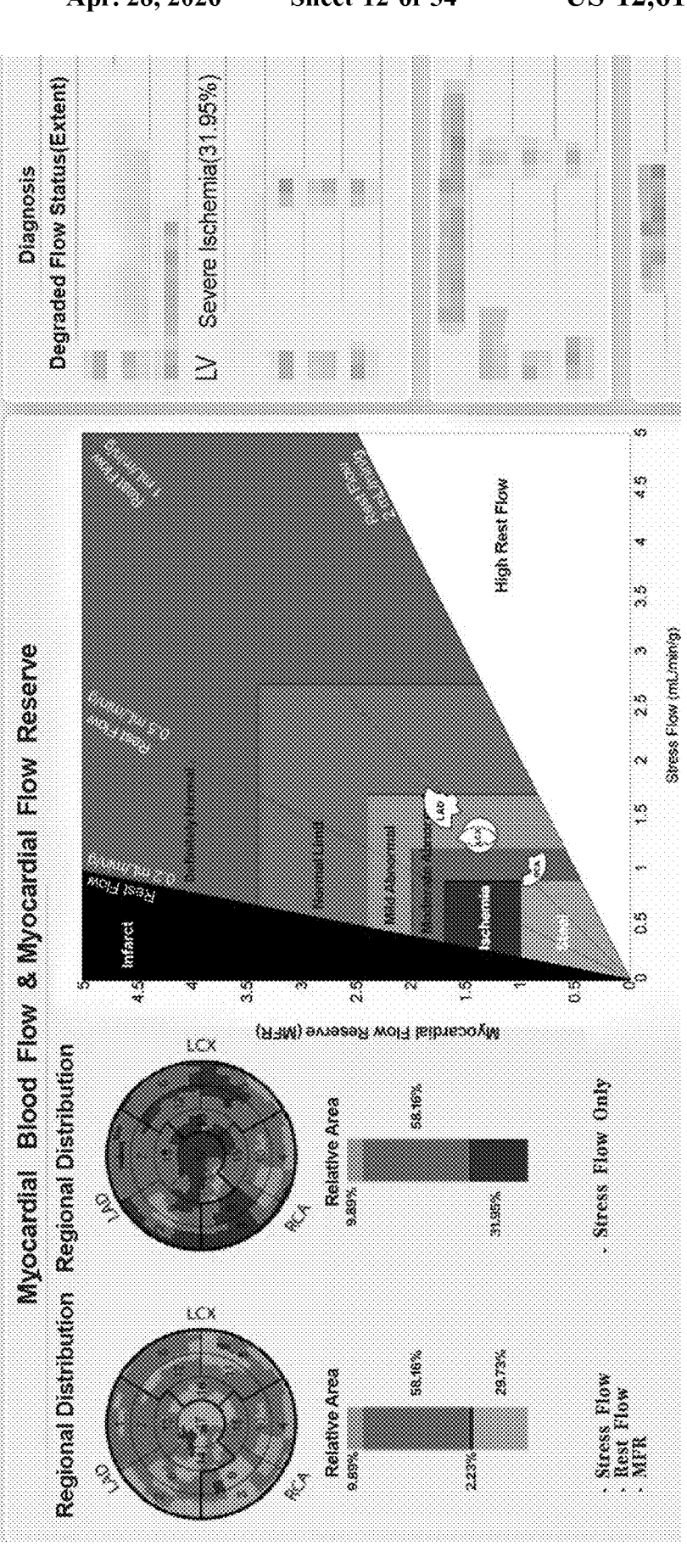

FIG. 7B is a diagram of myocardial flow reserve measured by a SPECT-CT instrument on Nov. 9, 2017. It shows that: the percentage of myocardial ischemia after using R7 for treatment was 31.95%.

Subject 3

The percentage of myocardial ischemia before using the old therapeutic apparatus for treatment was 6.35%.

The percentage of myocardial ischemia after using the old therapeutic apparatus for treatment was 5.69%.

The myocardial ischemia was reduced by 10.39% using the old therapeutic apparatus for treatment compared with that before treatment.

Figure 8A:
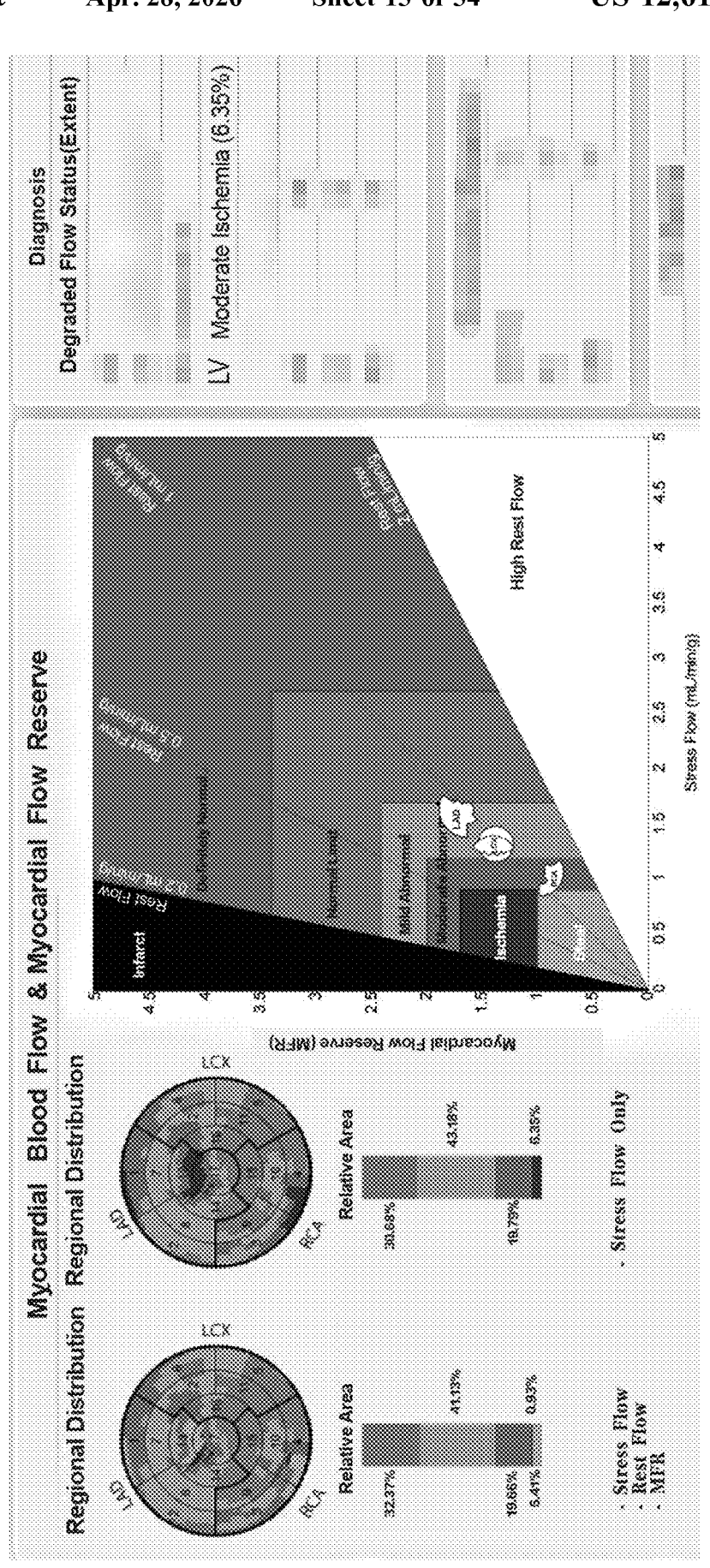

FIG. 8A is a diagram of myocardial flow reserve measured by a SPECT-CT instrument on Dec. 19, 2017. It shows that: the percentage of myocardial ischemia before using R7 for treatment was 6.35%.

Figure 8B:
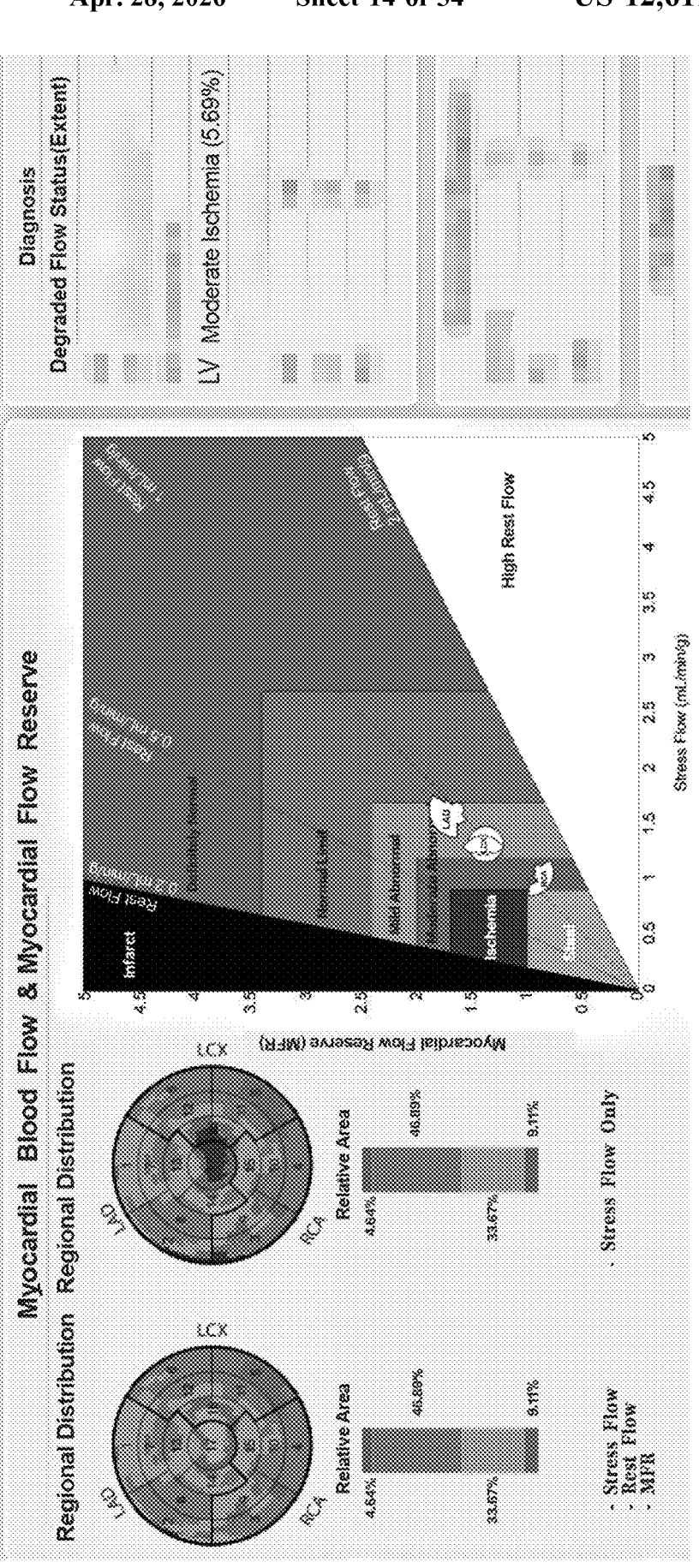

FIG. 8B is a diagram of myocardial flow reserve measured by a SPECT-CT instrument on Jun. 19, 2018. It shows that: the percentage of myocardial ischemia after using R7 for treatment was 5.69%.

Subject 4

The percentage of myocardial ischemia before using R7 for treatment was 21.12%.

The percentage of myocardial ischemia after using R7 for treatment was 0.76%.

The myocardial ischemia was reduced by 96.40% using R7 for treatment compared with that before treatment.

Figure 9A:
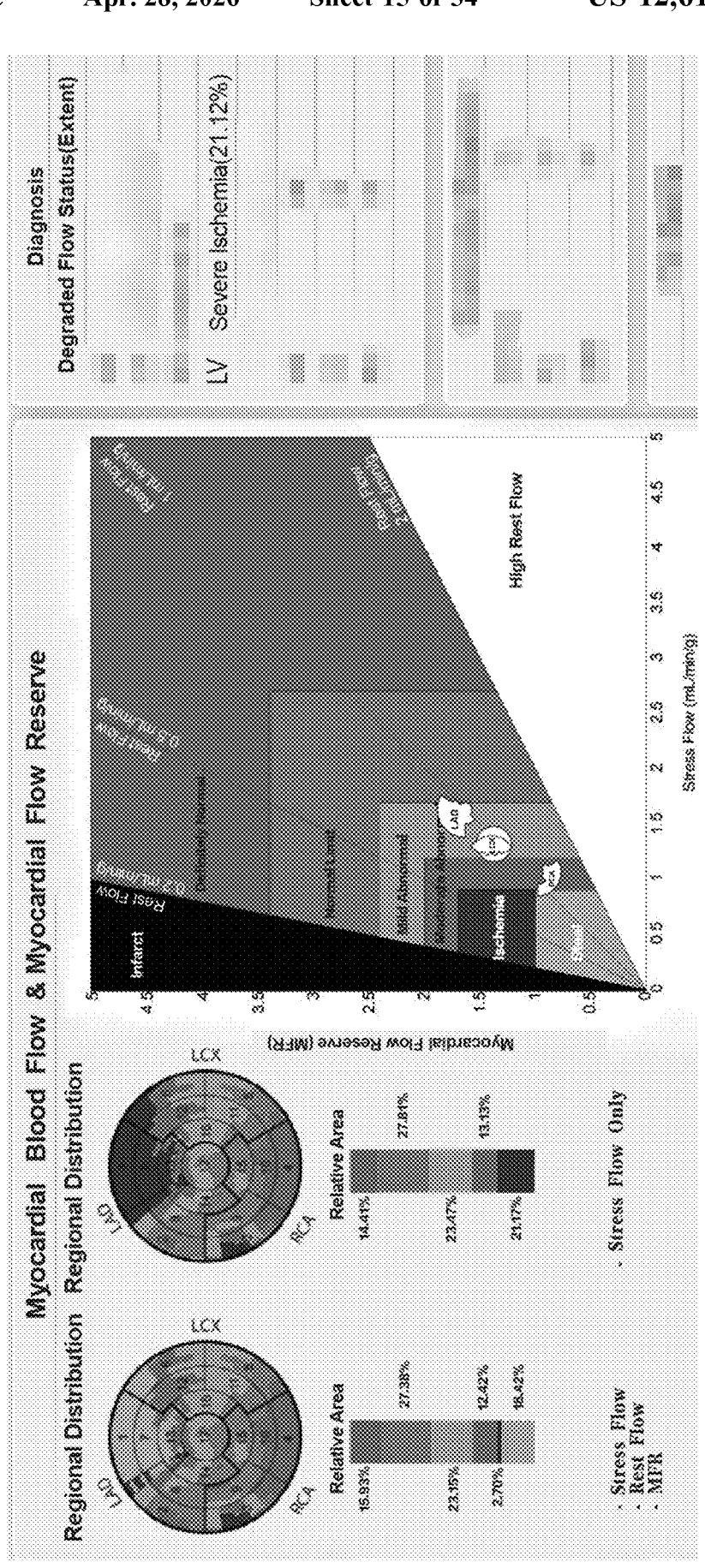

FIG. 9A is a diagram of myocardial flow reserve measured by a SPECT-CT instrument on Dec. 5, 2017. It shows that: the percentage of myocardial ischemia before using R7 for treatment was 21.12%.

Figure 9B:
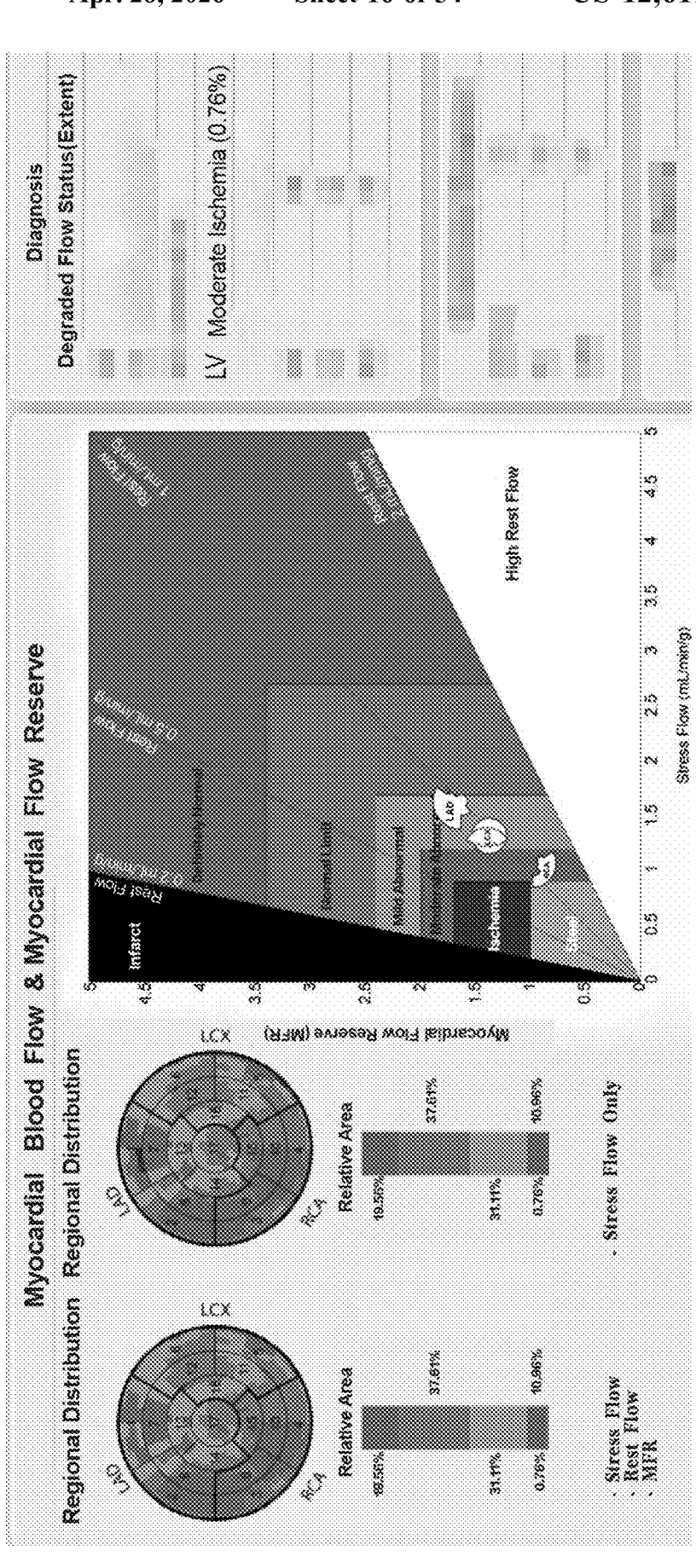

FIG. 9B is a diagram of myocardial flow reserve measured by a SPECT-CT instrument on Jul. 5, 2018. It shows that: the percentage of myocardial ischemia after using R7 for treatment was 0.76%.

Subject 5

The percentage of myocardial ischemia before using R7 for treatment was 10.37%.

The percentage of myocardial ischemia after using R7 for treatment was 0.

The myocardial ischemia was reduced by 100% using R7 for treatment compared with that before treatment.

Figure 10A:
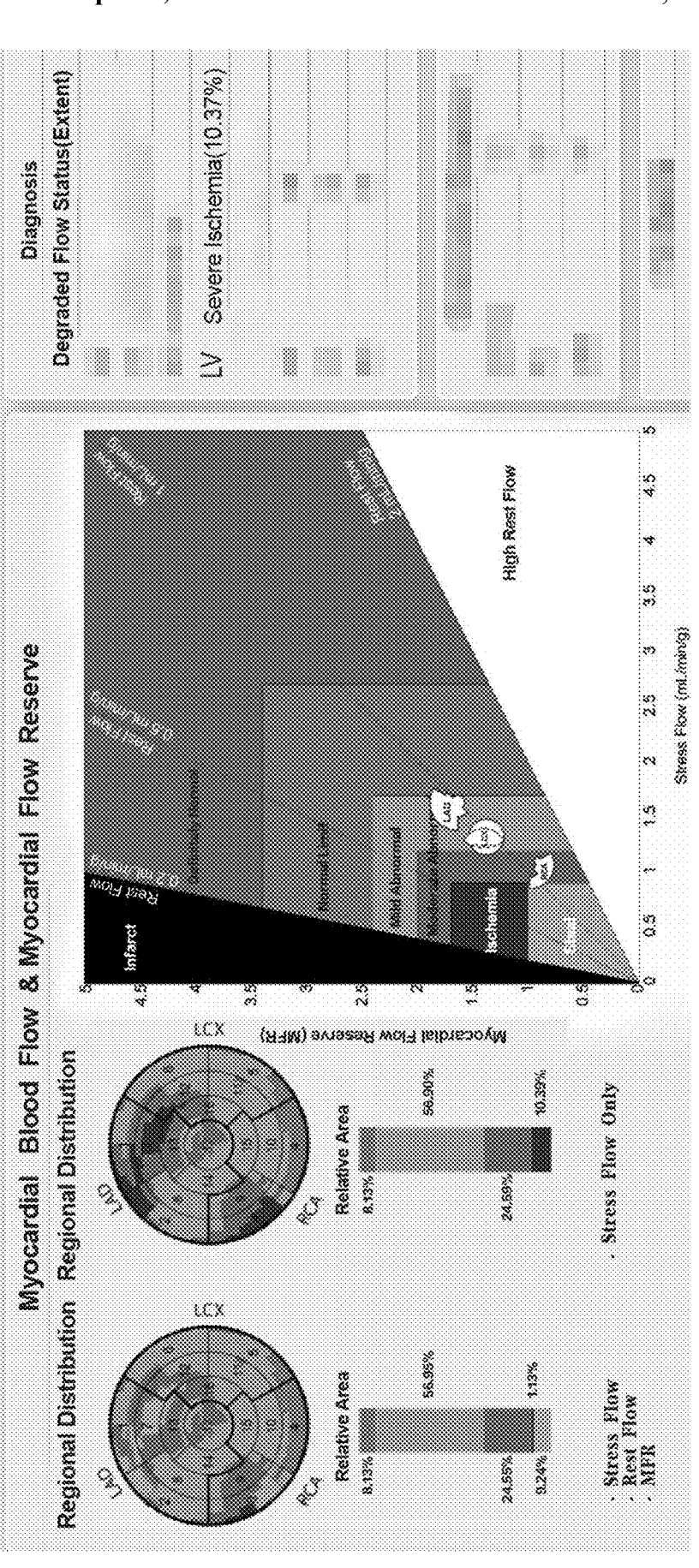

FIG. 10A is a diagram of myocardial flow reserve measured by a SPECT-CT instrument on Oct. 31, 2017. It shows that: the percentage of myocardial ischemia before using R7 for treatment was 10.37%.

Figure 10B:
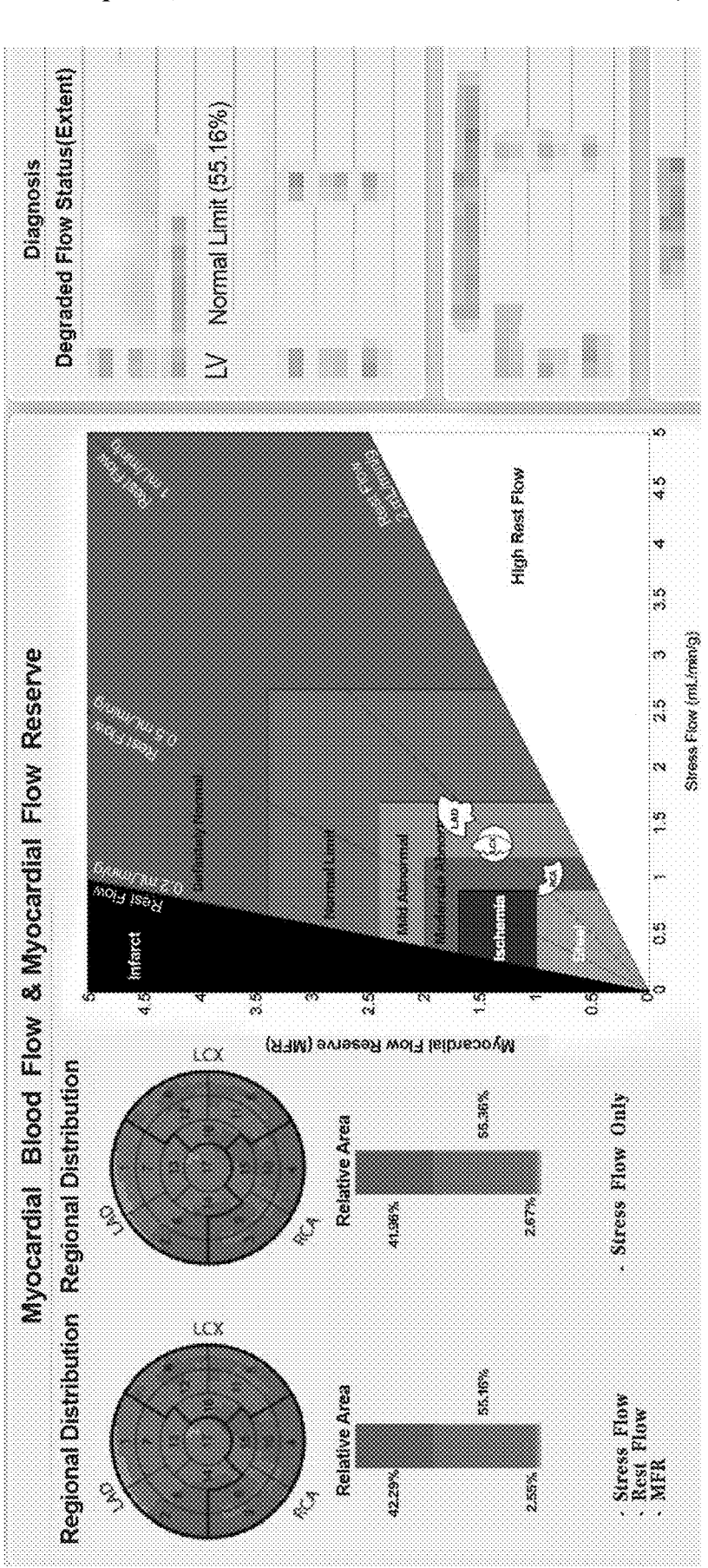

FIG. 10B is a diagram of myocardial flow reserve measured by a SPECT-CT instrument on May 8, 2018. It shows that: the percentage of myocardial ischemia after using R7 for treatment was 0.

Subject 6

The percentage of myocardial ischemia before using R7 for treatment was 33.76%.

The percentage of myocardial ischemia after using R7 for treatment was 8.88%.

The myocardial ischemia was reduced by 73.70% using R7 for treatment compared with that before treatment.

Figure 11A:
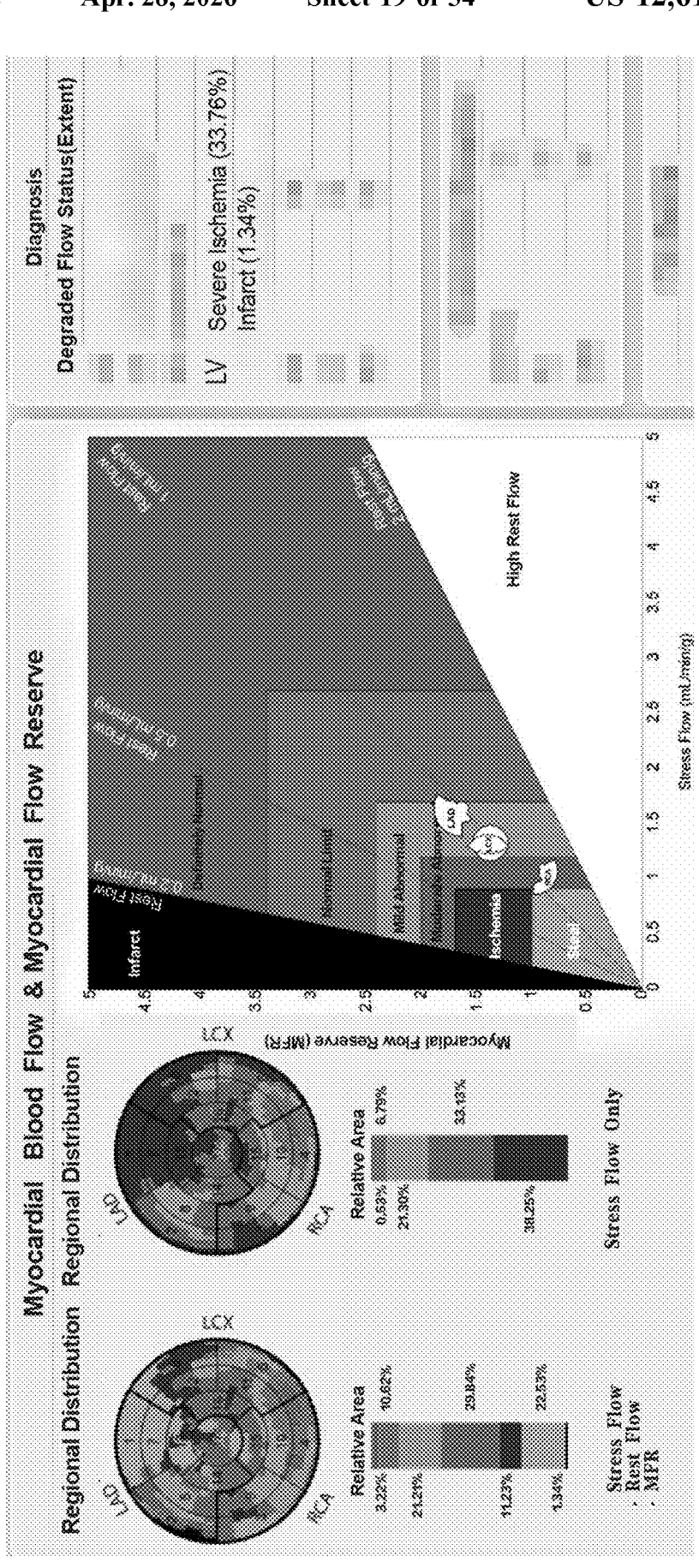

FIG. 11A is a diagram of myocardial flow reserve measured by a SPECT-CT instrument on Aug. 14, 2017. It shows that: the percentage of myocardial ischemia before using R7 for treatment was 33.76%.

Figure 11B:
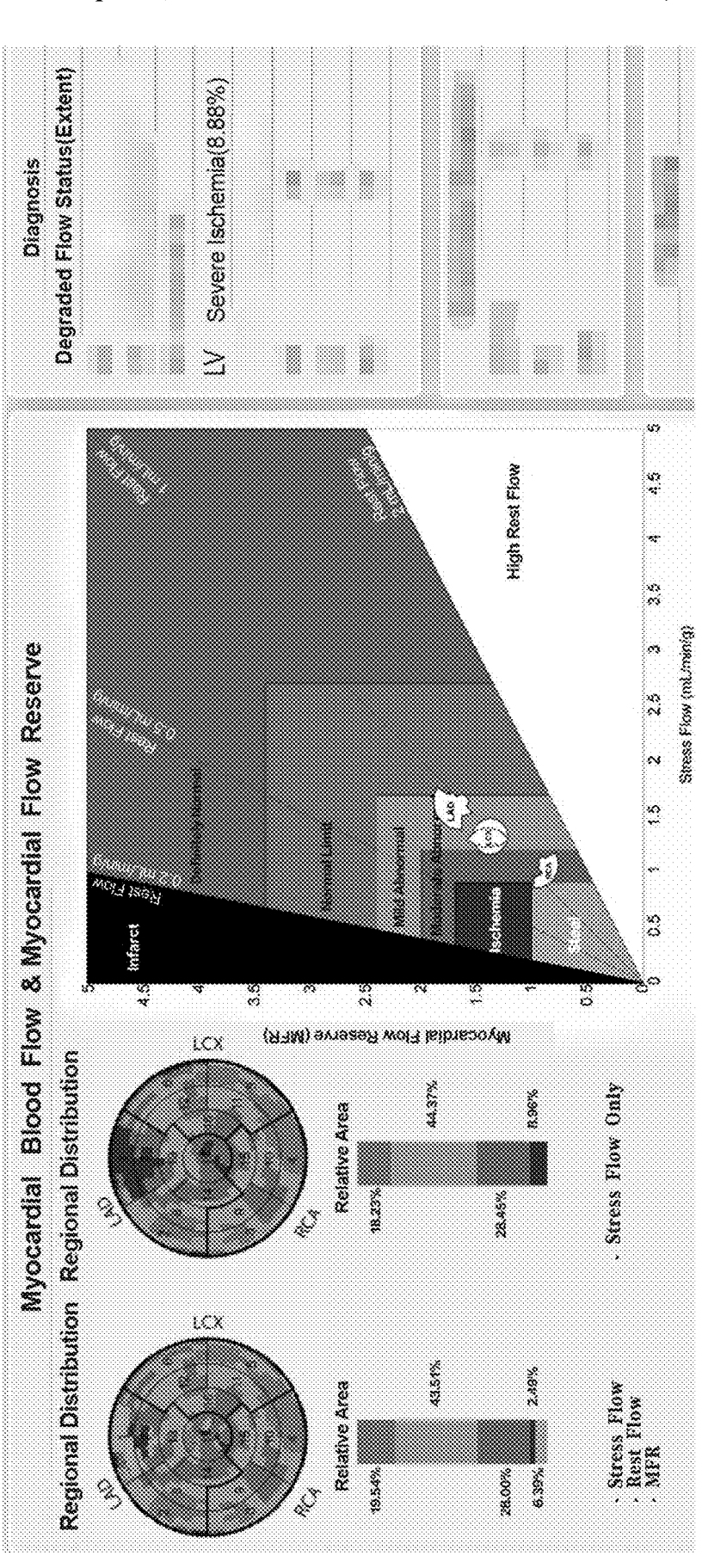

FIG. 11B is a diagram of myocardial flow reserve measured by a SPECT-CT instrument on Nov. 23, 2017. It shows that: the percentage of myocardial ischemia after using R7 for treatment was 8.88%.

Subject 7

The percentage of myocardial ischemia before using R7 for treatment was 9.52%.

The percentage of myocardial ischemia after using R7 for treatment was 0.

The myocardial ischemia was reduced by 100% using R7 for treatment compared with that before treatment.

Figure 12A:
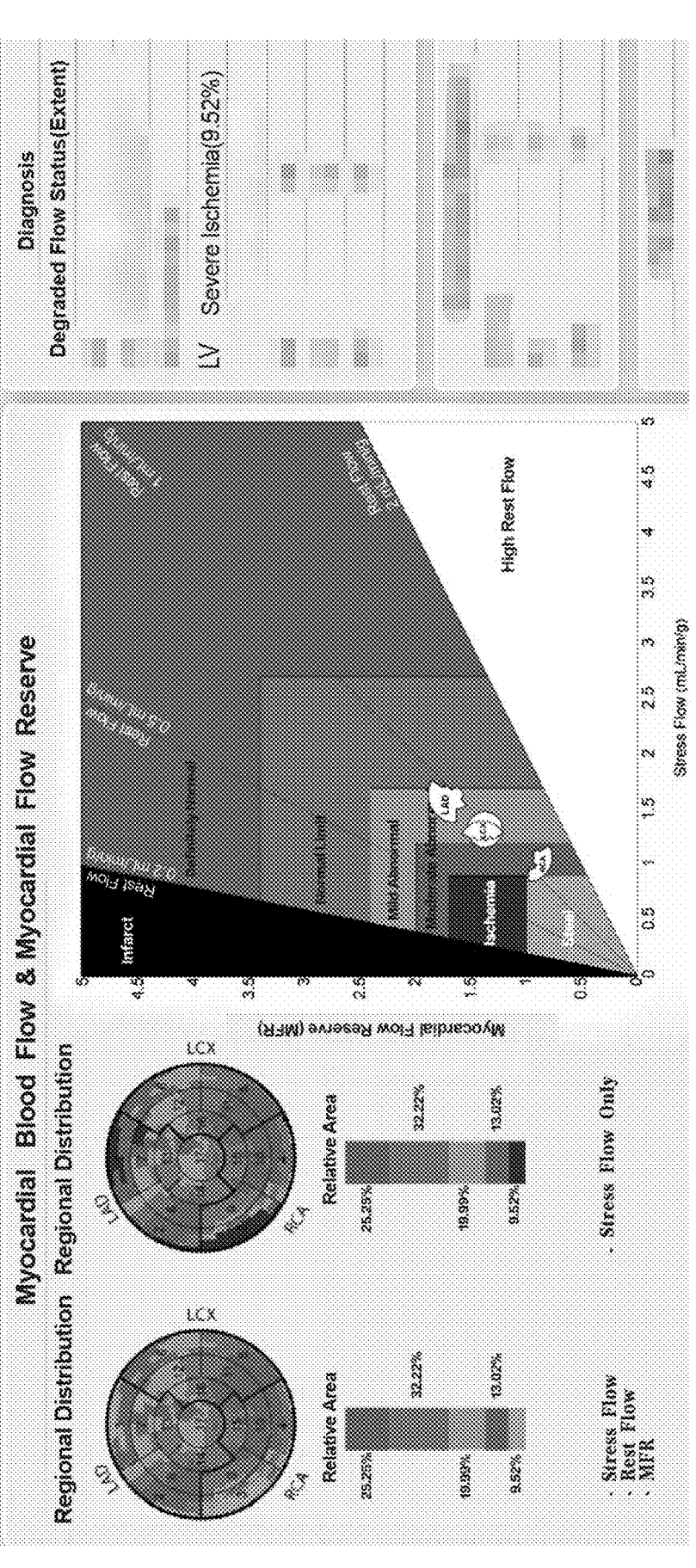

FIG. 12A is a diagram of myocardial flow reserve measured by a SPECT-CT instrument on Apr. 3, 2018. It shows that: the percentage of myocardial ischemia before using R7 for treatment was 9.52%.

Figure 12B:
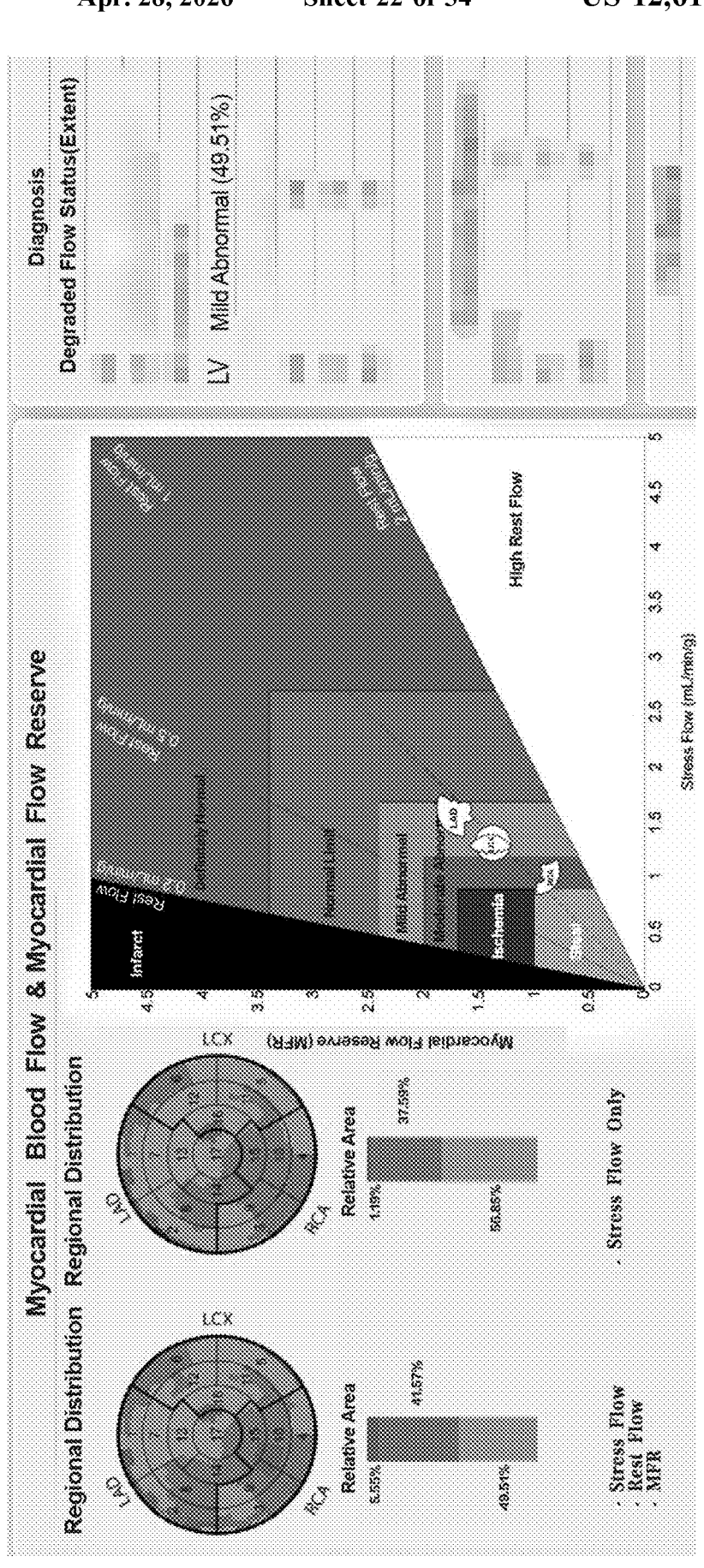

FIG. 12B is a diagram of myocardial flow reserve measured by a SPECT-CT instrument on Oct. 12, 2018. It shows that: the percentage of myocardial ischemia after using R7 for treatment was 0.

Subject 8

The percentage of myocardial ischemia before using R7 for treatment was 10.05%.

The percentage of myocardial ischemia after using R7 for treatment was 2.06%.

The myocardial ischemia was reduced by 79.5% using R7 for treatment compared with that before treatment.

Figure 13A:
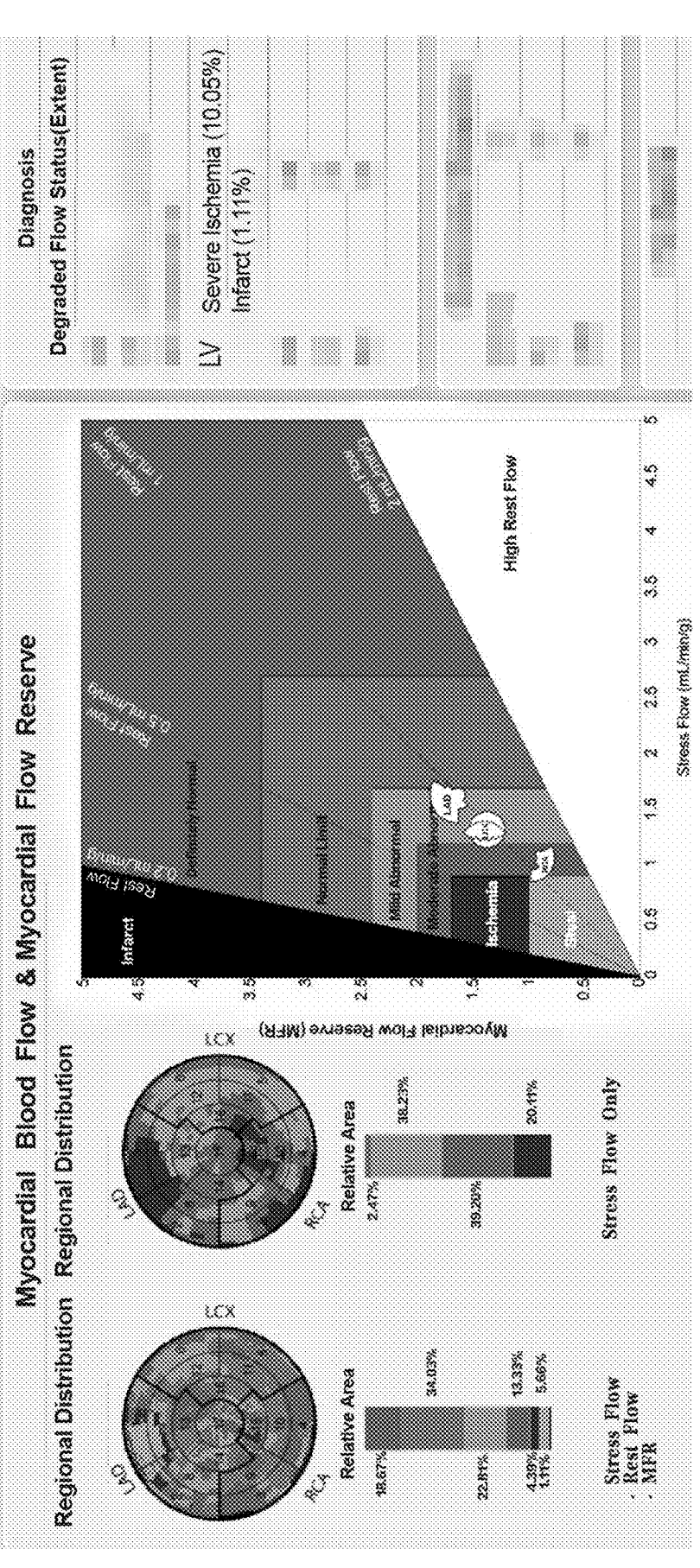

FIG. 13A is a diagram of myocardial flow reserve measured by a SPECT-CT instrument on Jul. 11, 2018. It shows that: the percentage of myocardial ischemia before using R7 for treatment was 10.05%.

Figure 13B:
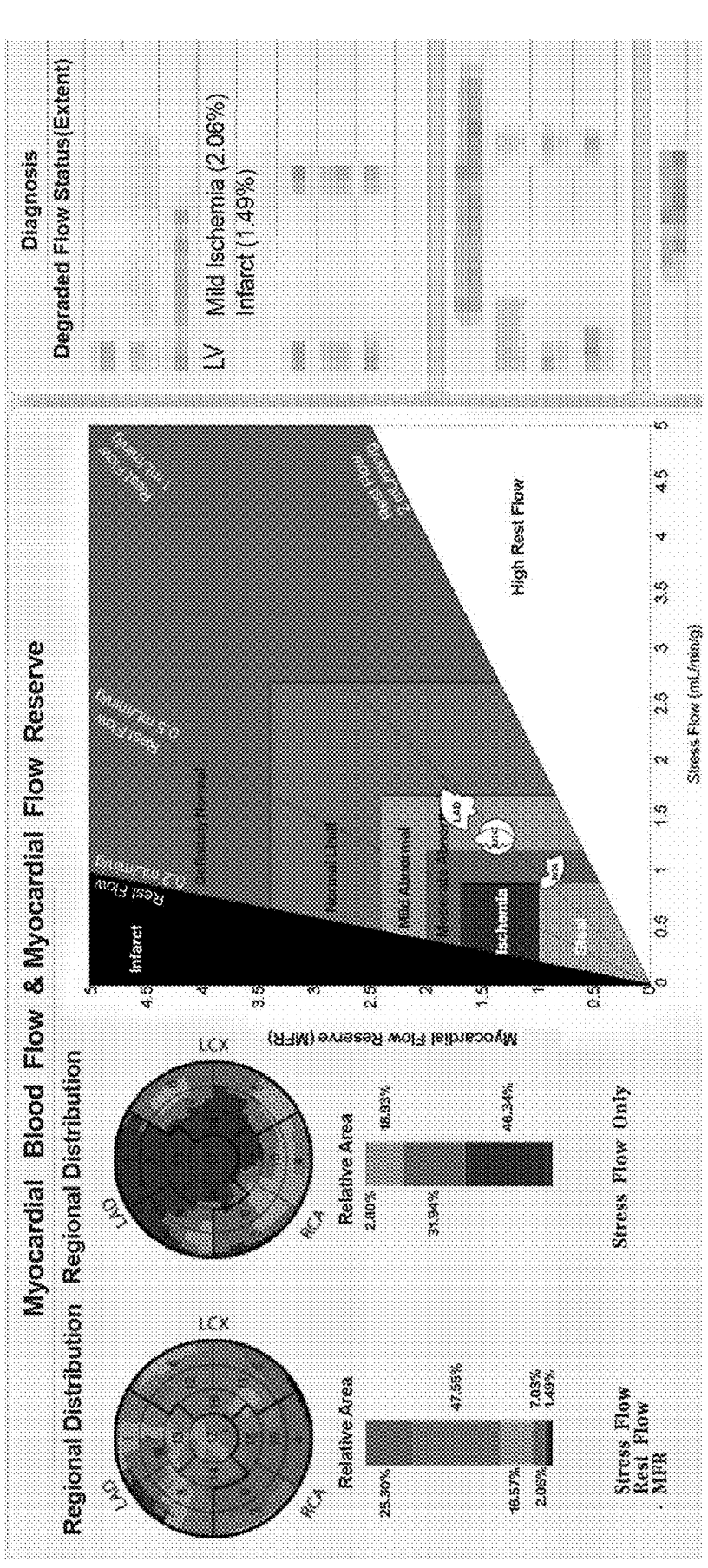

FIG. 13B is a diagram of myocardial flow reserve measured by a SPECT-CT instrument on Jul. 4, 2019. It shows that: the percentage of myocardial ischemia after using R7 for treatment was 2.06%.

Subject 9

The percentage of myocardial ischemia before using R7 for treatment was 8.79%.

The percentage of myocardial ischemia after using R7 for treatment was 2.21%.

The myocardial ischemia was reduced by 74.86% using R7 for treatment compared with that before treatment.

Figure 14A:
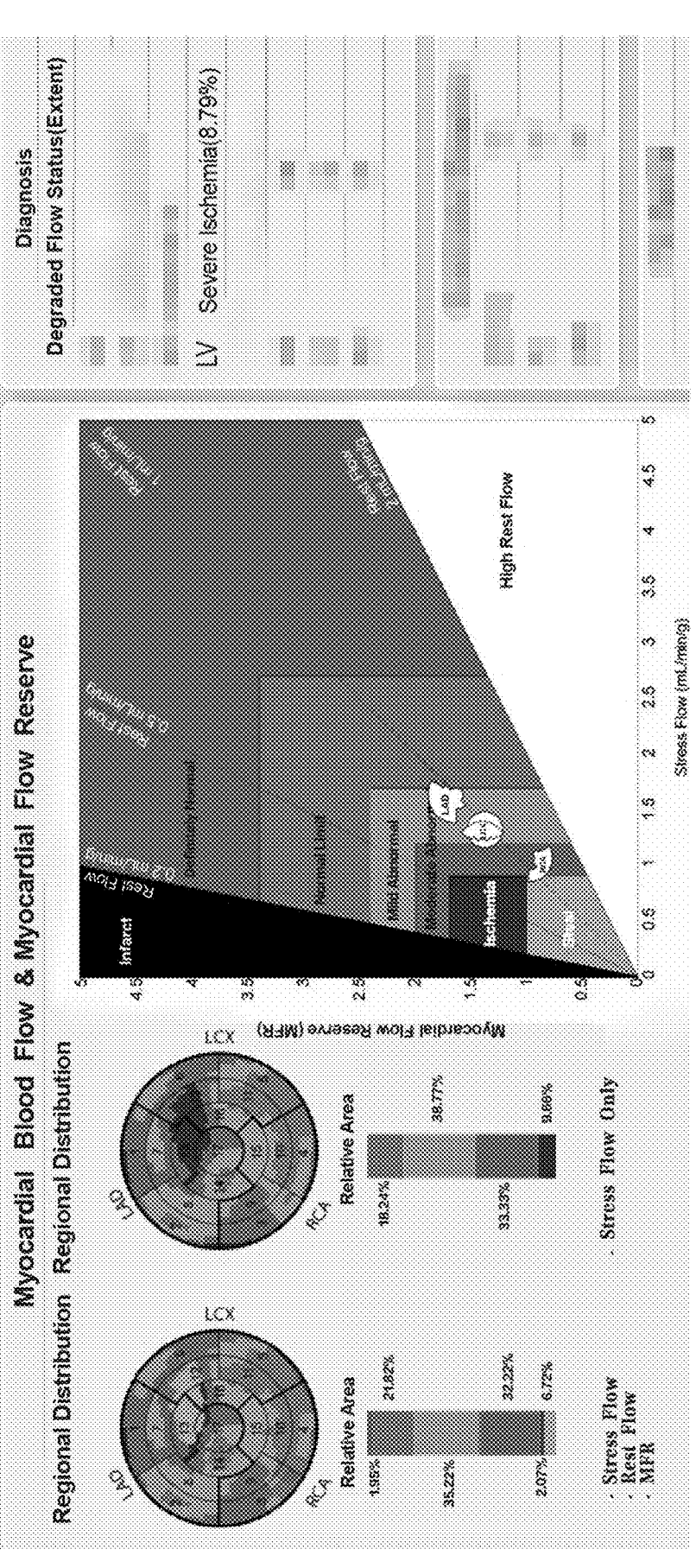

FIG. 14A is a diagram of myocardial flow reserve measured by a SPECT-CT instrument on Sep. 17, 2018. It shows that: the percentage of myocardial ischemia before using R7 for treatment was 8.79%.

Figure 14B:
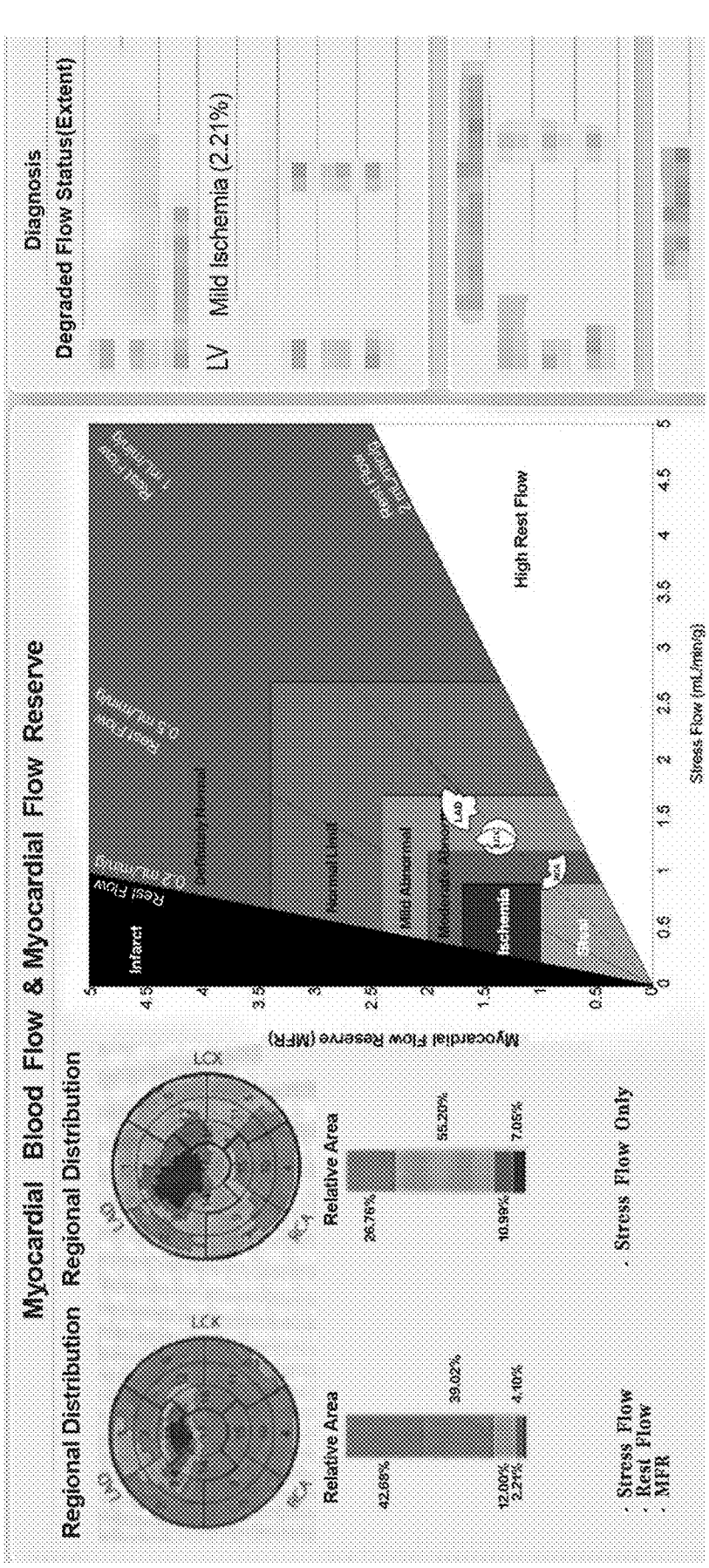

FIG. 14B is a diagram of myocardial flow reserve measured by a SPECT-CT instrument on Mar. 21, 2019. It shows that: the percentage of myocardial ischemia after using R7 for treatment was 2.21%.

Subject 10

The percentage of myocardial ischemia of the subject 10 before using R7 for treatment was 18.17%.

The percentage of myocardial ischemia after using R7 for treatment was 10.11%.

The myocardial ischemia was reduced by 44.36% using R7 for treatment compared with that before treatment.

Figure 15A:
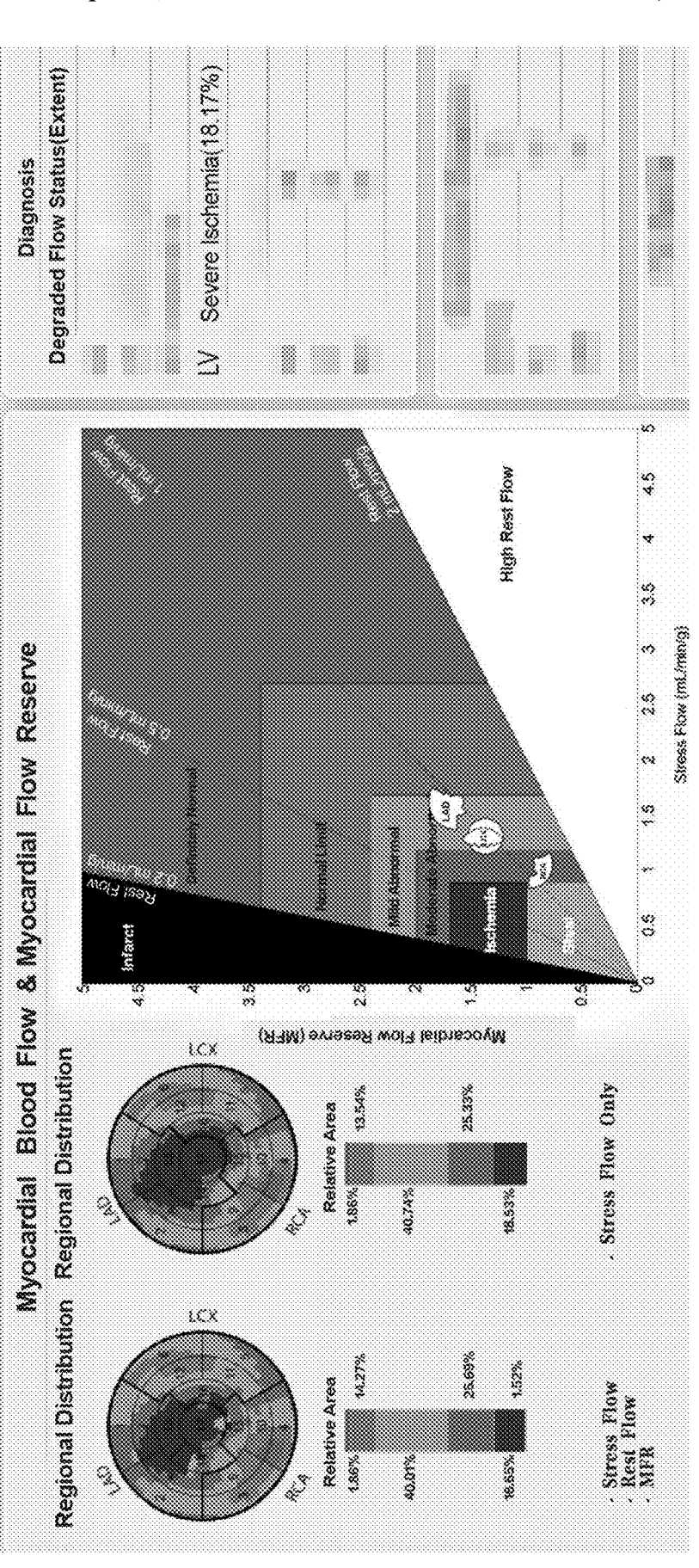

FIG. 15A is a diagram of myocardial flow reserve measured by a SPECT-CT instrument on May 29, 2019. It shows that: the percentage of myocardial ischemia of subject 10 before using R7 for treatment was 18.17%.

Figure 15B:
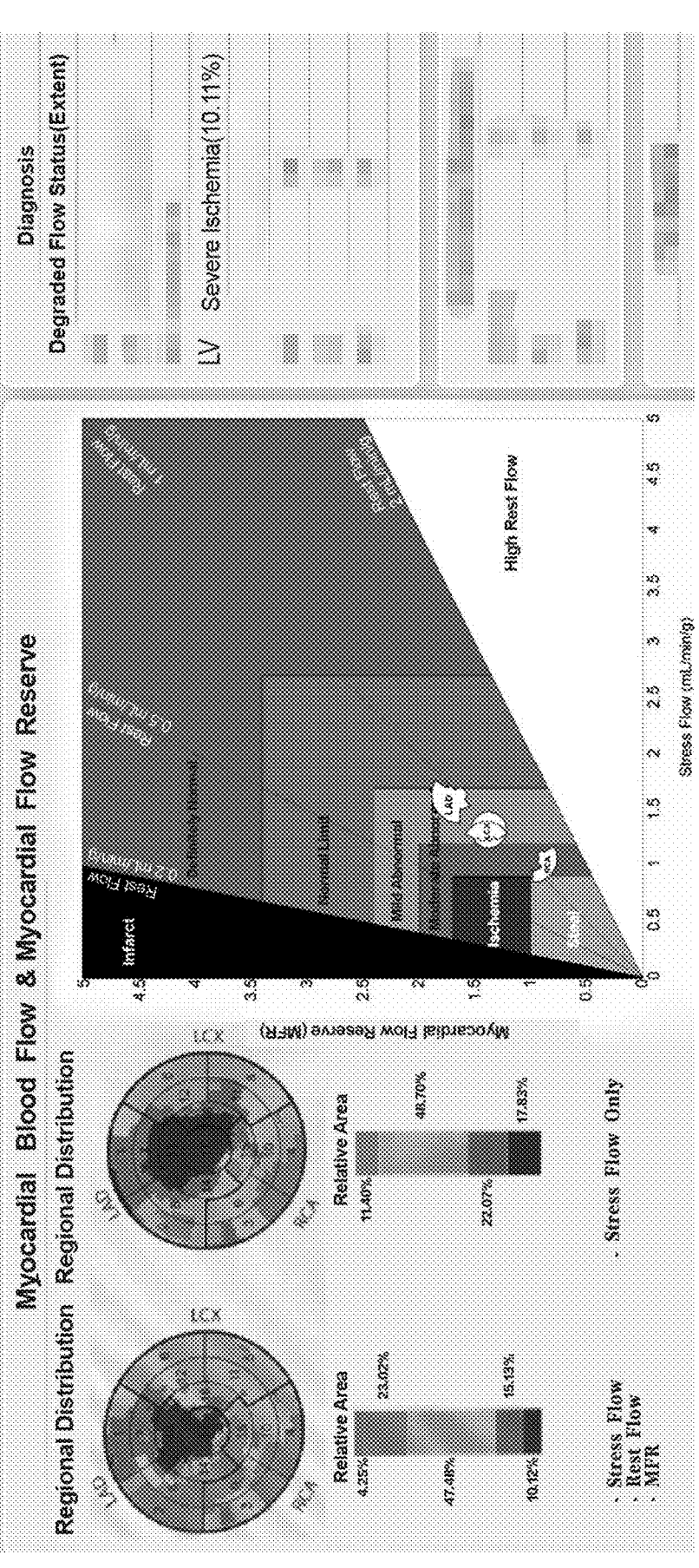

FIG. 15B is a diagram of myocardial flow reserve measured by a SPECT-CT instrument on Jun. 16, 2020. It shows that: the percentage of myocardial ischemia after using R7 for treatment was 10.11%.

Subject 11

The percentage of myocardial ischemia of the subject 11 before using R7 for treatment was 3.24%.

The percentage of myocardial ischemia after using R7 for treatment was 12.32%.

The myocardial ischemia was increased by 280.25% using R7 for treatment compared with that before treatment.

Figure 16A:
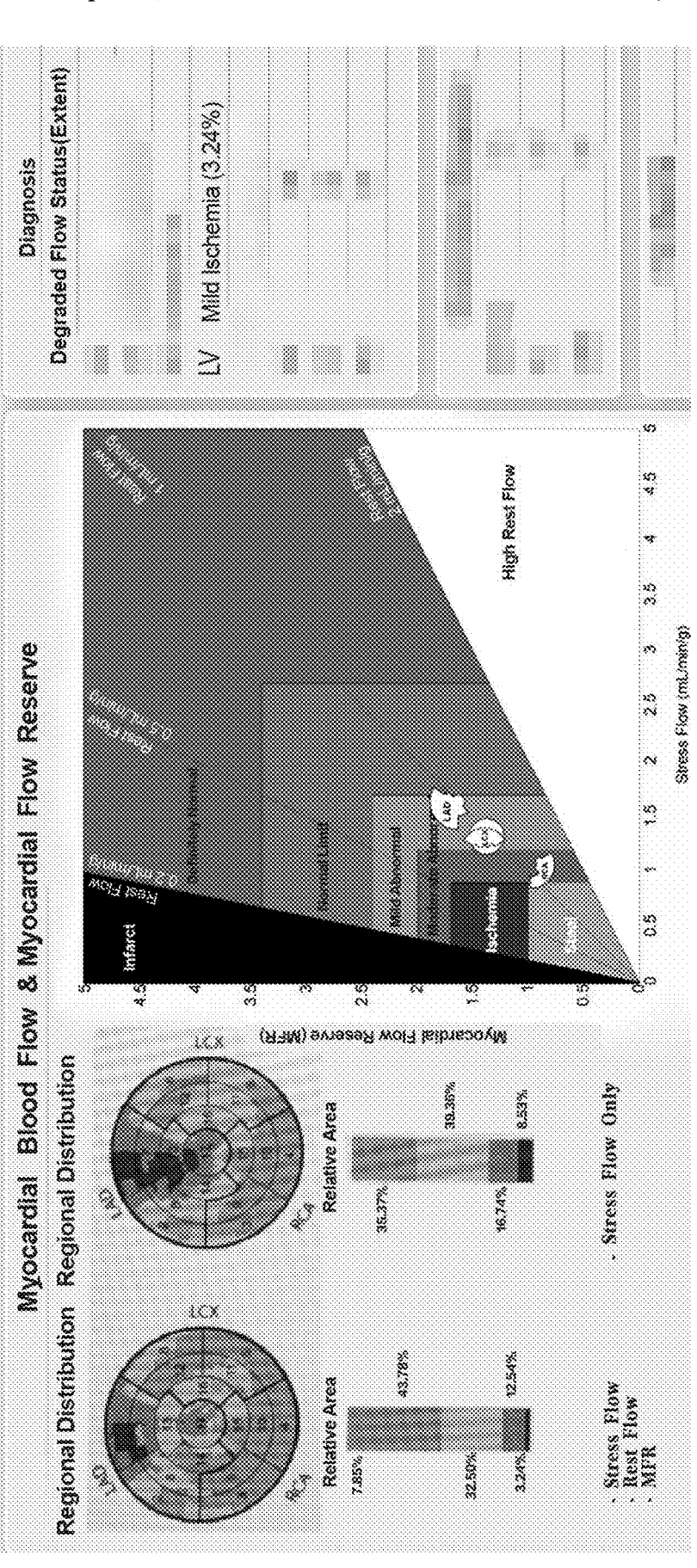

FIG. 16A is a diagram of myocardial flow reserve measured by a SPECT-CT instrument on Nov. 5, 2019. It shows that: the percentage of myocardial ischemia of a subject 11 before using R7 for treatment was 3.24%.

Figure 16B:
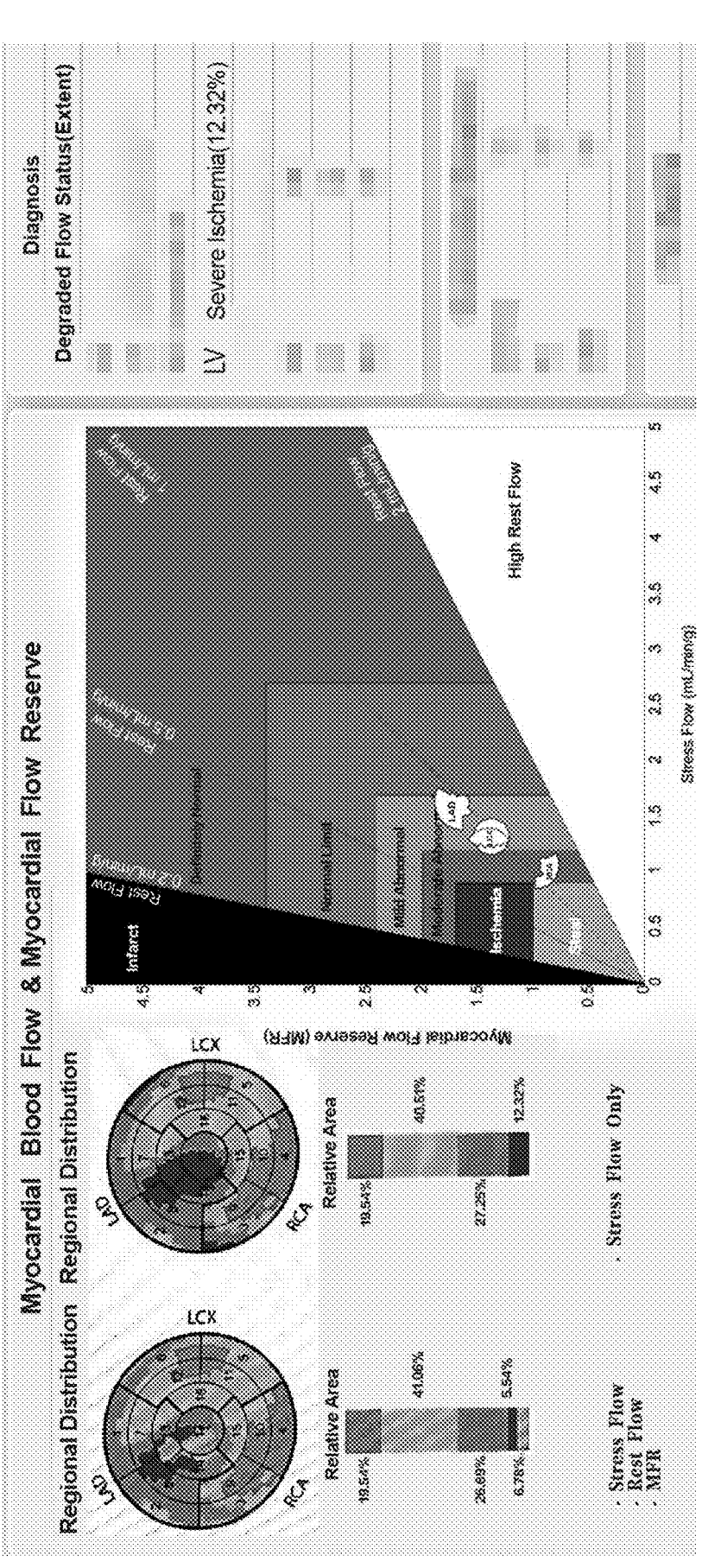

FIG. 16B is a diagram of myocardial flow reserve measured by a SPECT-CT instrument on Jun. 11, 2020. It shows that: the percentage of myocardial ischemia after using R7 for treatment was 12.32%.

Subject 12

The percentage of myocardial ischemia before using R7 for treatment was 18.06%.

The percentage of myocardial ischemia after using R7 for treatment was 35.84%.

The myocardial ischemia was increased by 98.45% using R7 for treatment compared with that before treatment.

Figure 17A:
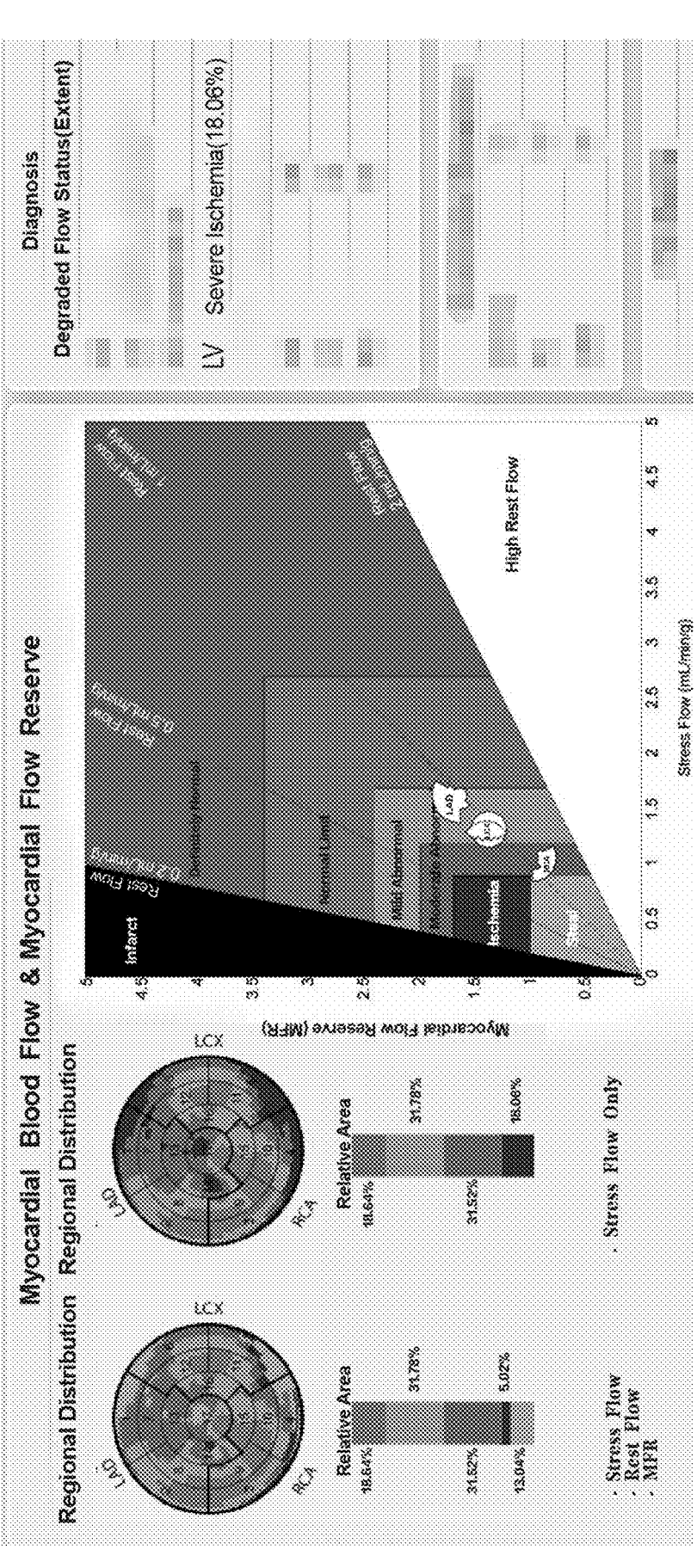

FIG. 17A is a diagram of myocardial flow reserve measured by a SPECT-CT instrument on Nov. 27, 2019. It shows that: the percentage of myocardial ischemia before using R7 for treatment was 18.06%.

Figure 17B:
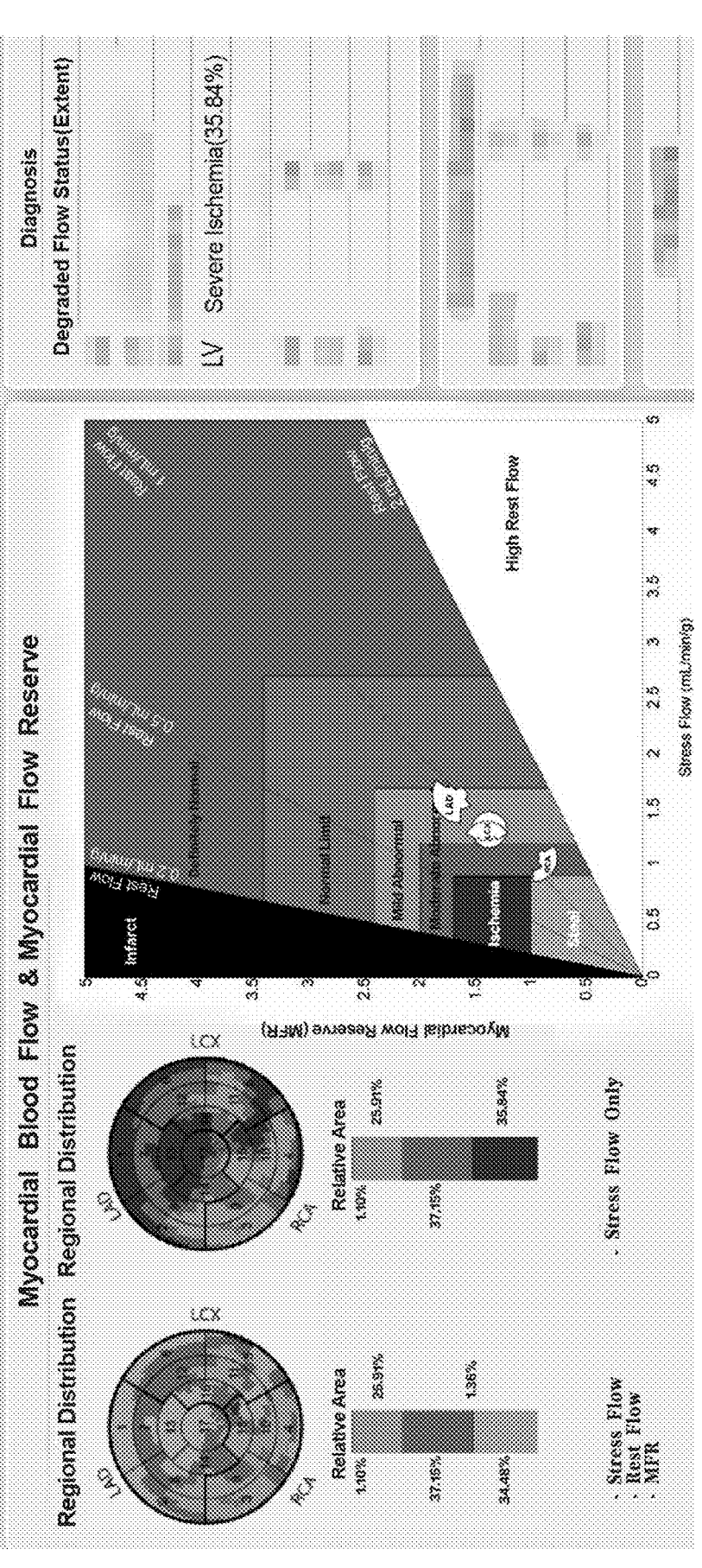

FIG. 17B is a diagram of myocardial flow reserve measured by a SPECT-CT instrument on Sep. 10, 2020. It shows that: the percentage of myocardial ischemia after using R7 for treatment was 35.84%.

Subject 13

The percentage of myocardial ischemia before using R7 for treatment was 59.19%.

The percentage of myocardial ischemia after using R7 for treatment was 98.51%.

The myocardial ischemia was increased by 66.43% using R7 for treatment compared with that before treatment.

Figure 18A:
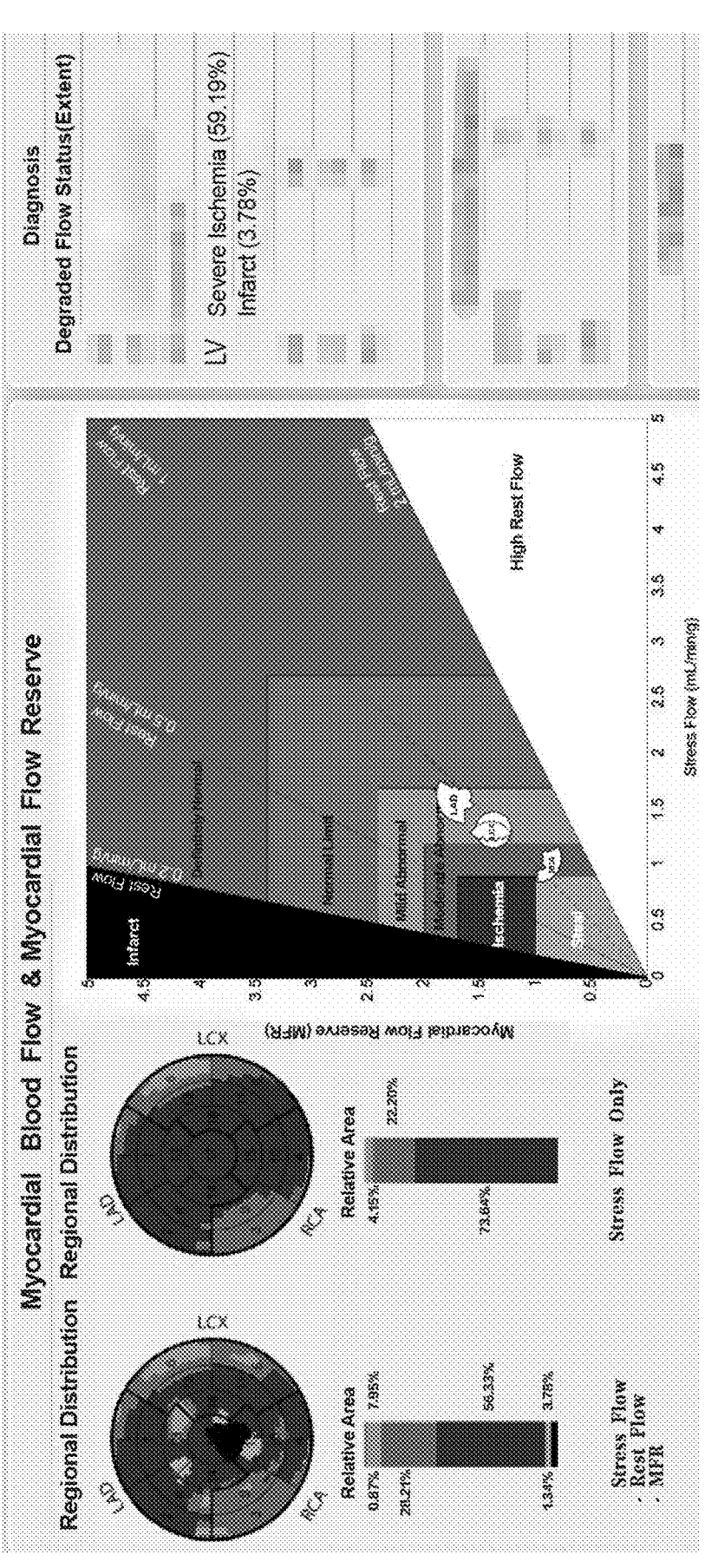

FIG. 18A is a diagram of myocardial flow reserve measured by a SPECT-CT instrument on Oct. 14, 2019. It shows that: the percentage of myocardial ischemia before using R7 for treatment was 59.19%.

Figure 18B:
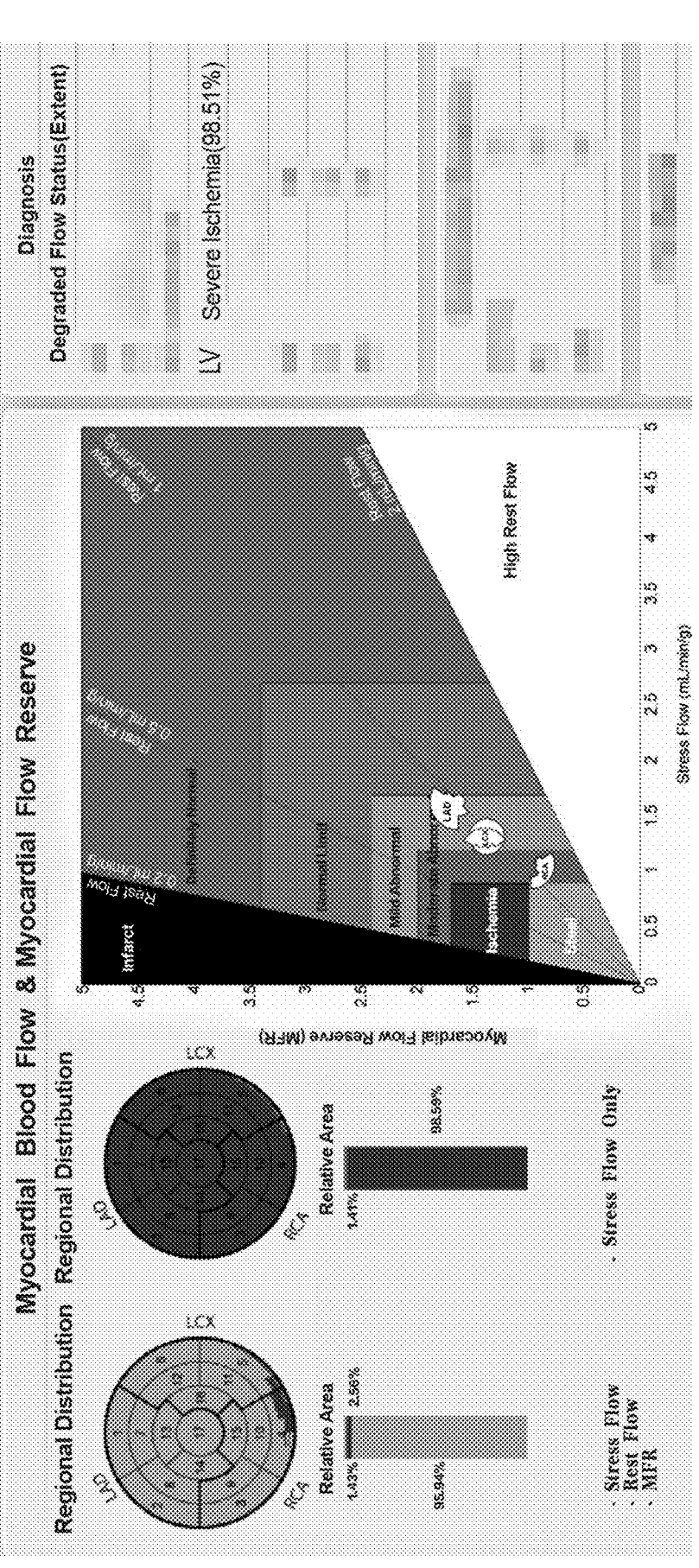

FIG. 18B is a diagram of myocardial flow reserve measured by a SPECT-CT instrument on Sep. 24, 2020. It shows that: the percentage of myocardial ischemia after using R7 for treatment was 98.51%.

Experiment Conclusion:

This shows that through comparison of the experimental test data above, the non-drug cardio-cerebrovascular disease therapeutic apparatus provided by the present invention can significantly improve myocardial ischemia of the patients with coronary heart disease and effectively restore blood perfusion. Current medical methods are limited in blood perfusion for restoring myocardial blood supply, and the technology has become a new technology for high-efficiency intervention of cardiovascular diseases.

Similarly, the applicant also discovered through research that, by using the non-drug cardio-cerebrovascular disease therapeutic apparatus provided by the present invention, through magnetic field action on human blood vessels especially acupoint accessories with rich effects and rich blood flow according to the characteristics of the pulse waveform disclosed and limited by the present invention, regeneration treatment of human cells can be significantly improved and significant effects are achieved. Compared with the prior art, the present invention realizes essential improvements in the patients with coronary heart disease and myocardial ischemia, and can be widely used for treating or improving symptoms of overall cardio-cerebrovascular diseases.

II. Comparative Experimental Verification of the Non-Drug Cardio-Cerebrovascular Disease Therapeutic Apparatus Provided by the Present Invention and the Prior Art (WO 2012/048203)

The technology disclosed by the prior art (WO 2012/048203) is a product of a previous generation ("old product"). After the old product, the applicant carried out continuous research and development according to users' using effect, and through continuous tests and comparisons, obtained the non-drug cardio-cerebrovascular disease therapeutic apparatus of the present invention (product code "R7") which achieves a better effect in treating cardio-cerebrovascular diseases.

Angina is a common symptom of cardio-cerebrovascular diseases. Therefore, in the comparison experiment of effects of cardio-cerebrovascular therapeutic apparatuses, the "Seattle Angina Questionnaire" in Table 2 below is often used to test the subjects' indicators so as to compare instrument therapeutic effects of the two test subjects:

TABLE 2

| SAQ-7 Seattle Angina Questionnaire |
| --- |

1. Below is a list of activities that people often do in a week. Although for some people with multiple diseases, it is difficult to define what limits them, please carefully check the activities listed below and explain how much you were limited due to chest pain, chest tightness, or angina in the past 4 weeks.

| Activity | Severe limit | Moderate limit | Mild limit | Slight limit | No limit | Limit for other reasons |
| --- | --- | --- | --- | --- | --- | --- |
| a. Walking on indoor flat ground | 1 point | 2 points | 3 points | 4 points | 5 points | 6 points |
| b. Gardening, vacuuming or carrying groceries | 1 point | 2 points | 3 points | 4 points | 5 points | 6 points |
| c. Lifting or moving heavy objects (such as furniture, a child) | 1 point | 2 points | 3 points | 4 points | 5 points | 6 points |

2. In the past four weeks, how many times on average did you have chest pain, chest tightness, or angina? I had chest pain, chest tightness, or angina . . .

| 4 times or more on a daily basis | 1-3 times on a daily basis | 3 times or more every week, but not every day | 1-2 times every week | 1 time for 1 week | None in the past 4 weeks |
| --- | --- | --- | --- | --- | --- |
| 1 point | 2 points | 3 points | 4 points | 5 points | 6 points |

3. In the past four weeks, how many times on average did you have to take nitroglycerin tablets for chest pain, chest tightness, or angina? I took nitroglycerin tablets . . .

| 4 times or more on a daily basis | 1-3 times on a daily basis | 3 times or more every week, but not every day | 1-2 times every week | 1 time for 1 week | None in the past 4 weeks |
| --- | --- | --- | --- | --- | --- |
| 1 point | 2 points | 3 points | 4 points | 5 points | 6 points |

4. In the past four weeks, to what extent did chest pain, chest tightness, or angina affect your enjoying life?

| Severe limit | Moderate limit | Mild limit | Slight limit | No limit |
| --- | --- | --- | --- | --- |
| 1 point | 2 points | 3 points | 4 points | 5 points |

5. If you have to live the rest of your life with your current chest pain, chest tightness or angina, what would you think?

| Absolutely unsatisfied | Frequently unsatisfied | Slightly satisfied | Mostly satisfied | Highly satisfied |
| --- | --- | --- | --- | --- |
| 1 point | 2 points | 3 points | 4 points | 5 points |

The applicant adopted item 2 in Table 2 above, used the "old therapeutic apparatus" in the prior art to conduct follow-up tests on 6 patients (test subjects) for 6 months, and obtained experiment data in Table 4 based on scores in Table 3.

TABLE 3

Comparison of Effects on Coronary Heart Disease between the Therapeutic Apparatus and the Old Therapeutic Apparatus Using "Angina stable state" Scores in the Seattle Angina Questionnaire as Basis In the past four weeks, how many times on average did you have chest pain, chest tightness, or angina? I had chest pain, chest tightness, or angina . . .

| 4 times or more on a daily basis | 1-3 times on a daily basis | 3 times or more every week, but not every day | 1-2 times every week | 1 time for 1 week | None in the past 4 weeks |
| --- | --- | --- | --- | --- | --- |
| 1 point | 2 points | 3 points | 4 points | 5 points | 6 points |

TABLE 4

| Scoring of Subjects after 6 Months (Experiment Data) | | | |
|---|---|---|---|
| Old therapeutic apparatus | | | |
| Patient | Before use | After use | Improvement |
| Zhang XX | 3 | 3 | 0 |
| Wang XX | 4 | 5 | 1 |
| Wang XX | 3 | 4 | 1 |
| Li XX | 3 | 4 | 1 |
| Wu XX | 1 | 3 | 2 |
| Gao XX | 1 | 2 | 1 |
| Average improvement | | | 1 |
| New therapeutic apparatus | | | |
| Patient | Before use | After use | Improvement |
| Tang XX | 3 | 6 | 3 |
| Huang XX | 2 | 6 | 4 |
| Wang XX | 4 | 6 | 2 |
| Gao XX | 2 | 6 | 4 |
| Wu XX | 1 | 4 | 4 |
| Wang XX | 2 | 6 | 4 |
| Zhao XX | 1 | 6 | 5 |
| Average improvement | | | 4.3 |

(The test results show that the subjects using the new therapeutic apparatus of the present invention achieve much better effect than those using the old therapeutic apparatus)

Experimental analysis data shows that: most of the improvement effect indicators are "1", and the best is "2" which is very few. Follow-up tests were conducted on 7 patients (part of the test subjects are the same) using the therapeutic apparatus of the present invention for 6 months, and the experiment data in Table 4 was obtained. It shows that most of the improvement effect indicators are "4", the worst is "2" and the best is "5".

Therefore, based on the comparison of technical effects between the therapeutic apparatus of the present invention and the prior art (WO2012/048203) (the original "old therapeutic apparatus" of the applicant) according to the experiment data in Table 4, it is easy for those skilled in the art to see that the technical effect achieved by the non-drug cardio-cerebrovascular disease therapeutic apparatus of the present invention is particularly significant.

Especially, for the non-drug cardio-cerebrovascular disease therapeutic apparatus provided by the present invention, the overall waveform characteristics of a pulse current waveform composed of the above waveform characteristics T1, T2, T3 and T4 are quite different from waveforms of existing magnetic field therapeutic apparatuses (including WO2012/048203), especially in the introduction of the waveform characteristics T3 and T4. Compared with waveform characteristics of the prior art, the non-drug cardio-cerebrovascular disease therapeutic apparatus has particularly significant technical characteristics and therefore achieves a significant technical effect.

The foregoing displays and describes basic principles, main features, and advantages of the present invention. A person skilled in the art may understand that the present invention is not limited to the foregoing embodiments. Descriptions in the embodiments and this specification merely illustrate the principles of the present invention. Various modifications and improvements are made in the present invention without departing from the spirit and the scope of the present invention, and such modifications and improvements shall fall within the protection scope of the present invention. The protection scope of the present invention is defined by the appended claims.

What is claimed is:

1. A non-drug cardio-cerebrovascular disease therapeutic apparatus comprising:
  a power supply device;
  a pulse current generator connected with the power supply device to generate a pulse current; and
  a pulse magnetic field generator connected with the pulse current generator,
  wherein the pulse magnetic field generator comprises a magnetic head, the magnetic head comprises an electromagnet and a coil, and the coil is connected with the pulse current generator and receives the pulse current to generate a pulse electromagnetic field that may be applied to a patient, wherein a waveform diagram of the pulse current comprises four characteristic bands in a cycle range of 360° and reciprocates circularly:
    an abrupt-rising band T1 where a current intensity I(t) abruptly rises, wherein a highest value thereof is slightly lower than a maximum value Imax of an output current;
    a first slow-rising band T2 where the current intensity I(t) slowly rises to the maximum value Imax;
    an abrupt-decreasing band T3 where the current intensity I(t) abruptly decreases, wherein a minimum value Imin thereof is slightly higher than a minimum value (Imin) of the output current; and
    a slow-decreasing band T4 where the current intensity I(t) slowly decreases to the minimum value (Imin),
  wherein a sequence of the pulse current in each cycle is T1, T2, T3 and T4, and
  wherein a waveform formula of the pulse current is:
  $I(t)=I*(1-e(t/z))$, in a 0-180° interval $=I*(e(t/z))$, in a 180-360° interval where:
    z is a time factor, with a range of (0.001-0.003),
    f=30 Hz,
    t is a time range of 0-0.03333 second, and
    I is the current intensity provided by a power supply, and is 0-100 mA.

2. The non-drug cardio-cerebrovascular disease therapeutic apparatus according to claim 1, wherein 0.01 second$\leq \tau \leq$0.025 second.

3. The non-drug cardio-cerebrovascular disease therapeutic apparatus according to claim 1, wherein 0 mA$\leq$I$\leq$90 mA.

4. The non-drug cardio-cerebrovascular disease therapeutic apparatus according to claim 1, wherein 0.001$\leq$z$\leq$0.003.

5. The non-drug cardio-cerebrovascular disease therapeutic apparatus according to claim 1, wherein z=0.002.

6. The non-drug cardio-cerebrovascular disease therapeutic apparatus according to claim 1, wherein an electromagnetic wave generator applies the pulse electromagnetic field to Laogong acupoint of a hand and/or Yongquan acupoint of a foot of the patient.

7. The non-drug cardio-cerebrovascular disease therapeutic apparatus according to claim 1, wherein the pulse current generator includes an ARM processor.

8. The non-drug cardio-cerebrovascular disease therapeutic apparatus according to claim 1, wherein the apparatus further comprises a D/A module which converts a waveform digital signal sent by an ARM processor into an analog pulse current signal so that the magnetic head generates the pulse electromagnetic field.

9. The non-drug cardio-cerebrovascular disease therapeutic apparatus according to claim 1, wherein the power supply device further comprises a current manager.

10. The non-drug cardio-cerebrovascular disease thera-
peutic apparatus according to claim 1, wherein
T1 and T2 increase monotonically and smoothly, and T3
and T4 decrease monotonically and smoothly.

\* \* \* \* \*